(12) United States Patent
Tajima

(10) Patent No.: US 8,163,183 B2
(45) Date of Patent: Apr. 24, 2012

(54) MAGNETIC PARTICLE PARALLEL PROCESSING APPARATUS PERMITTING REPEATED USE OF CONTAINER AND METHOD OF MAGNETIC PARTICLE PARALLEL PROCESSING PERMITTING REPEATED USE OF CONTAINER

(75) Inventor: Hideji Tajima, Matsudo (JP)

(73) Assignee: Universal Bio Research Co., Ltd., Chiba (JP)

( * ) Notice: Subject to any disclaimer, the term of this patent is extended or adjusted under 35 U.S.C. 154(b) by 278 days.

(21) Appl. No.: 12/448,635

(22) PCT Filed: Feb. 6, 2008

(86) PCT No.: PCT/JP2008/051923
§ 371 (c)(1),
(2), (4) Date: Jan. 19, 2010

(87) PCT Pub. No.: WO2008/096776
PCT Pub. Date: Aug. 14, 2008

(65) Prior Publication Data
US 2010/0137165 A1 Jun. 3, 2010

(30) Foreign Application Priority Data
Feb. 7, 2007 (JP) .................................. 2007-28592

(51) Int. Cl.
*B01L 3/02* (2006.01)
*B03C 1/00* (2006.01)
*G01N 1/00* (2006.01)
*G01N 35/02* (2006.01)

(52) U.S. Cl. ........ 210/695; 210/222; 436/177; 436/526; 422/509; 422/527

(58) Field of Classification Search .................. 210/222, 210/695; 436/177, 526; 422/509, 527
See application file for complete search history.

(56) References Cited

U.S. PATENT DOCUMENTS
5,702,950 A 12/1997 Tajima
(Continued)

FOREIGN PATENT DOCUMENTS
JP 8-62224 A 3/1996
(Continued)

OTHER PUBLICATIONS
International Preliminary Report on Patentability for PCT/JP2008/051923, Apr. 2009.*
(Continued)

*Primary Examiner* — David A Reifsnyder
(74) *Attorney, Agent, or Firm* — Haynes and Boone, LLP

(57) ABSTRACT

To provide a magnetic particle parallel processing apparatus permitting repeated use of a container, and a method of magnetic particle parallel processing permitting repeated use of a container, with which the rate of repeated use of a container is enhanced to thereby achieve a saving in the working space and a saving in the working time. The apparatus comprises: at least one reaction container; a liquid disposal tank; a reagent etc. feeder with at least one flow channel for feeding at least one type of liquid selected from the group consisting of two or more types of solutions and a magnetic particle suspension according to the processing content, at a given amount and at a given timing, to the reaction container; and a magnetic separator which has at least one processing nozzle with a distal end insertable into the reaction container and the liquid disposal tank, for sucking and discharging a liquid through the distal end, and which also has a magnetic means capable of applying a magnetic field to the interior of the distal end to thereby attract magnetic particles contained in the liquid inside the distal end to the inner wall thereof to effect separation of the magnetic particles, and canceling the magnetic field to thereby release the attracted magnetic particles and re-suspend the same in a liquid.

16 Claims, 10 Drawing Sheets

U.S. PATENT DOCUMENTS

| | | |
|---|---|---|
| 5,895,631 A | 4/1999 | Tajima |
| 6,143,250 A | 11/2000 | Tajima |
| 6,602,474 B1 | 8/2003 | Tajima |
| 6,637,053 B1 | 10/2003 | Tajima |
| 6,691,748 B1 | 2/2004 | Tajima |
| 2002/0007054 A1 | 1/2002 | Sakurai et al. |

FOREIGN PATENT DOCUMENTS

| | | |
|---|---|---|
| JP | 8-320274 A | 12/1996 |
| JP | 11-266864 A | 10/1999 |
| JP | 2001-194372 | 7/2001 |
| JP | 2005-91105 A | 4/2005 |
| JP | 2007-028592 | 2/2007 |
| WO | WO 97/05492 A1 | 2/1997 |
| WO | WO2008/096776 A1 | 8/2008 |

OTHER PUBLICATIONS

International Search Report issued May 13, 2008, by the ISA/JP, in connection with International Application No. PCT/JP2008/051923 (English translation thereof included in cite No. B8, namely WO2008/096776 A1).

Written Opinion issued May 13, 2008, by the ISA/JP, in connection with International Application No. PCT/JP2008/051923.

Second Written Opinion issued Feb. 10, 2009 by the IPEA/JP, in connection with International Application No. PCT/JP2008/051923.

* cited by examiner (a)

(b)

(a)

(b)

MAGNETIC PARTICLE PARALLEL PROCESSING APPARATUS PERMITTING REPEATED USE OF CONTAINER AND METHOD OF MAGNETIC PARTICLE PARALLEL PROCESSING PERMITTING REPEATED USE OF CONTAINER

CROSS REFERENCE

This application is a United States national phase application of co-pending international patent application number PCT/JP2008/051923, filed Feb. 6, 2008, which claims priority to Japanese patent application number 2007-28592, filed Feb. 7, 2007, the disclosures of which are incorporated herein by reference.

TECHNICAL FIELD

The present invention relates to a magnetic particle parallel processing apparatus permitting repeated use of a container, and a method of magnetic particle parallel processing permitting repeated use of a container.

BACKGROUND ART

Conventionally, in order to process a biological substance such as DNA, solutions such as; a magnetic particle suspension for use in the processing, a specimen solution, a reagent solution required for the processing of the specimen, a washing liquid, and the like are dispensed from a group of reagent etc. containers previously storing these solutions, and arrayed in accordance with the order of processing, in two or more liquid storage units for use in the processing, using a dispenser device. After the solutions have been arrayed, the magnetic particle suspension is sucked from and discharged into the first liquid storage unit using at least one processing nozzle which has at least one distal end insertable into the respective liquid storage units, for sucking and discharging a liquid through the distal end. By so doing, the magnetic particles such as magnetized silica and the target DNA contained in the specimen are captured, and a magnetic field is applied to the interior of the processing nozzle to thereby attract the magnetic particles to the inner wall of the distal end of the processing nozzle to effect separation of the magnetic particles. The residual liquid after the attraction of the magnetic particles is discharged into the first liquid storage unit, and then the magnetic particles are moved to the second liquid storage unit while being attracted to the inner wall of the distal end. After the movement, the distal end of the processing nozzle is inserted into the second liquid storage unit, and the solution stored in the storage unit is sucked and discharged in a state where the magnetic field has been cancelled, to thereby re-suspend the magnetic particles in the liquid. Through repetitive sucking and discharging, the magnetic particles are washed. After the washing operation, the liquid is sucked and a magnetic field is applied to the distal end to attract the magnetic particles to the inner wall thereof. Then, the residual liquid is discharged into the second liquid storage unit. Next, the washed magnetic particles are moved to the third liquid storage unit while being attracted to the inner wall. After the movement, the distal end of the processing nozzle is inserted into the third liquid storage unit, and the dissociation solution stored in the storage unit is sucked and discharged, to thereby dissociate the DNA captured on the magnetic particles from the magnetic particles. By so doing, a DNA solution can be obtained (Patent Documents 1 and 2).

As described above, in the conventional processing of a biological substance using magnetic particles, first, liquid storage units of a number equal to the number of steps of the processing are prepared, and liquids such as a solution required for processing are dispensed and arrayed by the respective steps. After the solutions have been arrayed, the liquid contained in each liquid storage unit is respectively sucked with or without repetitive sucking and discharging using the processing nozzle. Then, a magnetic field is applied to thereby attract the magnetic particles to the inner wall of the distal end to effect separation of the magnetic particles. The residual liquid is discharged into each liquid storage unit, and then the processing nozzle is moved to the next liquid storage unit while the magnetic particles are being attracted to the inner wall, followed by repetition of similar processing operations for a number of times of the processing steps.

In this manner, in the conventional processing, two or more containers corresponding to the number of the processing steps need to be prepared, in addition to the containers previously storing the reagent or other substances, and the reagent or other substances need to be dispensed and arrayed therein in advance. In particular, in the case of simultaneous processing of a large number of specimens such as specimens extracted from 96 subjects, for example, arrays of the number of steps each having 96 wells in a matrix form (8 rows×12 columns) need to be additionally prepared and arranged. For this reason, there has been a problem in that a large working space may be required, and the working efficiency in terms of space may be lowered.

Moreover, in the conventional processing, after the reagent or other substances required for processing have been dispensed into the respective liquid storage units of a number equal to the number of steps, the nozzle of the dispenser device is fitted with a distal end for processing, to start execution of the processing. Furthermore, since the processing of each liquid storage unit is shifted to the next liquid storage unit while the liquid used in each liquid storage unit is discharged into the liquid storage unit, it takes time until the completion of the processing due to; the time for dispensing the reagent or other substances into each liquid storage unit, the time for sucking the reagent or other substances and attracting the magnet particles, and the time for discharging the residual liquid taken at each step. Therefore, there has been a problem in that a lengthy working time may be required, and the working efficiency in terms of time may be impaired.

In response to this, the inventor of this application has invented a vessel with an inside bottom formed in an appropriate shape so that the whole amount of a liquid contained in the vessel can be reliably sucked using the distal end of a dispensing nozzle (Patent Document 3), and has shown that the use of this invention enables reliable processing of a predetermined amount of liquid without processing an excessive liquid amount exceeding a specified liquid amount for compensating for residual liquid loss in each liquid storage unit. This has led to a finding of the inventor in which the use of this invention enables improvement in the working efficiency of processing using magnetic particles.

[Patent Document 1] Japanese Unexamined Patent Publication No. Hei 8-62224

[Patent Document 2] Japanese Unexamined Patent Publication No. Hei 8-320274

[Patent Document 3] International Patent Publication No. WO 1997/005492

DISCLOSURE OF THE INVENTION

[Problems to be Solved by the Invention]

Therefore, it is a first object of the present invention to provide a magnetic particle parallel processing apparatus permitting repeated use of a container, and a method of magnetic particle parallel processing permitting repeated use of a container, with which the number of containers or liquid storage units for use in the processing of magnetic particles can be reduced to enhance the rate of repeated use of the container to thereby achieve a saving in the working space.

It is a second object of the present invention to provide a magnetic particle parallel processing apparatus permitting repeated use of a container, and a method of magnetic particle parallel processing permitting repeated use of a container, with which the parallel processing of magnetic particles can be performed to thereby achieve a saving in the working time.

It is a third object of the present invention to provide a magnetic particle parallel processing apparatus permitting repeated use of a container, and a method of magnetic particle parallel processing permitting repeated use of a container, which are capable of reliable and precise processing and suitable for automization.

[Means for Solving the Problem]

A first aspect of this invention is a magnetic particle parallel processing apparatus permitting repeated use of a container, comprising: at least one reaction container capable of storing a liquid to be processed; a liquid disposal tank capable of Storing a liquid to be disposed or allowing the liquid to pass through; a reagent etc. feeder with at least one flow channel for feeding at least one type of liquid selected from the group consisting of two or more types of solutions and a magnetic particle suspension according to the processing content, at a given amount and at a given timing, to the reaction container; and a magnetic separator which has at least one processing nozzle with a distal end insertable into the reaction container and the liquid disposal tank, for sucking and discharging a liquid through the distal end, and which also has a magnetic means capable of applying a magnetic field to the interior of the distal end to thereby attract magnetic particles contained in the liquid inside the distal end to the inner wall thereof to effect separation of the magnetic particles, and canceling the magnetic field to thereby release the attracted magnetic particles and re-suspend the same in a liquid, wherein the distal end of the processing nozzle is relatively movably provided between the reaction container and the liquid disposal tank.

Here, the volume of the reaction container is, for example, about several ten microliters to several thousand microliters. Accordingly, the liquid volume to be handled is smaller than this, and thus is about several microliters to several thousand microliters. Hence, the volume of the distal end needs to be formed to be equal to or larger than the volume of the reaction container, and is, for example, about several ten microliters to several thousand microliters. The reaction container is formed from an organic substance such as polypropylene, polyester, polyethylene, or an acrylic resin, or an inorganic substance such as a glass, ceramics, or a metal.

When two or more of such reaction containers are provided, the distal ends of processing nozzles can be inserted into the reaction containers all at once by providing equal array pitches (center-to-center dimension) between the reaction containers and between the processing nozzles. The reaction container is preferably provided with a temperature controller which controls so as to heat or cool the interior of the container.

The term "selected liquid" means a liquid containing one or two types of liquid selected from the group consisting of various reagent solutions, a washing liquid, a specimen solution, and a magnetic particle suspension, according to the processing content. The specimen solution may be excluded from the solution to be selected by the reagent etc. feeder, and may be stored in a container which is relatively movable with respect to the distal end of the processing nozzle, similarly to the reaction container. "The liquid to be disposed is allowed to pass through" by providing, for example, a discharge outlet at the bottom of the liquid disposal tank.

The term "magnetic particle" refers to a particle having a magnetic property. The size is, for example, about one nanometer to several ten micrometers. The size, the mass, the material, the structure (single domain, having a surface covered with various coating materials, or the like), the character (paramagnetism, superparamagnetism, ferromagnetism, ferrimagnetism, magnitude of magnetism, or the like) thereof can be determined in accordance with the purpose of the processing. The material is made of ferric hydroxide, iron oxide hydrate, iron oxide, mixed iron oxide, iron, $\gamma$-$Fe_2O_3$, $Fe_3O_4$, or the like. The magnetic particle can be obtained by coating the material with various coating materials. The coating materials can include organic substances yielding various functional groups, ionic substances yielding ions, surface stabilizers for preventing aggregation or precipitation induced by a magnetic field (such as aliphatic di-, or polycarboxylic acids, substitution products and derivatives thereof), specific binding substances (such as ligands and receptors), and pharmacological activators. Alternatively, nonmagnetic carriers, for example, inorganic substances such as silica, a glass, ceramics, and a metal, or organic substances such as cellulose, an agarose gel, a rubber, and nylon, may also be used as magnetic particles by magnetization through adhesion, embedding, or binding of a magnetic material.

The term "ligand" refers to a molecule that binds to a specific receptor. Examples thereof can include genetic materials such as a nucleic acid, proteins, sugars, sugar chains, peptides, and other biological substances, which are, for example, agonists for and antagonists against a cytoplasmic receptor, poisonous substances (toxins and venoms), viral epitopes, hormones, hormone receptors, peptides, enzymes, enzyme substrates, lectins, sugars, oligonucleotides, polynucleotides, oligosaccharides, and antibodies. They may be either natural or artificial. The "receptor" means a substance having a binding property for such a ligand. Examples thereof include genetic materials such as a nucleic acid, proteins, sugars, sugar chains, peptides, and other biological substances. More specific examples of the combination between a receptor and a ligand include nucleic acid/complementary nucleic acid, maltose-binding protein/maltose, enzyme/substrate, antigen/antibody of various types (for example, biotin/avidin and biotin/streptavidin), IgG/protein A, and ATP-binding protein/ATP.

The "given amount" is set so that the total amount of liquids to be stored in the reaction container become smaller than the volume of the reaction container. The "given timing" means a timing set in accordance with the sucking, discharging, or moving operation of the processing nozzle.

The magnetic separator is provided with a bottom landing detector which can detect that the point of the distal end of the magnetic separator has abutted on the inside bottom of the container. As a result the whole amount of the liquid can be smoothly and reliably sucked from the reaction container or other containers.

The distal end of the flow channel of the reagent etc. feeder may be attached to the reaction container, or may be relatively movably provided with respect to the reaction container.

A second aspect of this invention is a magnetic particle parallel processing apparatus permitting repeated use of a container, wherein the reagent etc. feeder has two or more reagent etc. storage units for previously storing various solutions and a magnetic particle suspension required for processing, the flow channel has a distal end insertable into the reaction container, the various solutions and the magnetic particle suspension are discharged from the reagent etc. storage units through the distal end, and the distal end of the flow channel is relatively movably provided with respect to the reaction container.

The "reagent etc. feeder" may be configured such that, for example; a tank serving as the reagent etc. storage unit storing respective solutions is switched by a valve to be connected to a flow channel, and the flow channel is provided for each container so that a fluid from the tank can be discharged only in one direction by using a pump; or a liquid can be discharged from a cylinder through the flow channel by pushing a plunger which is slidably provided in a cylinder serving as the reagent etc. storage unit storing each solution. Moreover there may be provided; a reagent etc. storage unit with two or more reagent etc. storage containers for previously storing various solutions required for processing, and a magnetic particle suspension storage container for previously storing a magnetic particle suspension, serving as the reagent etc. storage unit, and a dispenser device with at least one dispensing nozzle serving as the flow channel having a distal end insertable into the reaction container and the reagent etc. storage unit, for sucking and discharging a liquid through the distal end, wherein the reaction container, the reagent etc. storage unit, and the dispensing nozzle are relatively provided in a movable manner therebetween.

If the distal end of the flow channel is relatively movably provided with respect to the reaction container, the arrangement may be such that, when the distal end of the processing nozzle is moved to a position where it is insertable into the liquid disposal tank, the distal end of the flow channel can be moved to a position where it is insertable into the reaction container while retaining the former position.

The magnetic particle suspension storage container for storing the magnetic particle suspension is preferably provided with an agitation mechanism for suspending magnetic particles to be stored in a liquid. The agitation mechanism comprises, for example, a projection in the container which projects from the inner wall of the container towards the rotation axis passing through the container, and a mechanism for rotating the container about the rotation axis. In this case, a liquid contained in the container is agitated by linking the container with the rotation mechanism.

A third aspect of this invention is a magnetic particle parallel processing apparatus permitting repeated use of a container, wherein the reaction container is provided on a transfer pathway of the distal end of the flow channel, and the reaction container and the liquid disposal tank are provided on a transfer pathway of the distal end of the processing nozzle.

The reaction container is provided to commonly exist on both of the transfer pathway of the distal end of the flow channel and the transfer pathway of the distal end of the processing nozzle. Therefore, if the reaction container is fixed, the transfer pathway of the distal end of the flow channel and the transfer pathway of the distal end of the processing nozzle intersect with each other at the reaction container, and the position of the reaction container is the feeding position of solutions or the like, as well as being the processing position of the processing nozzle. The intersection angle between the transfer pathways is appropriately determined according to; the arrangement of the flow channel, the processing nozzle, or the reaction container, and the respective transfer pathways. If the respective wells and the nozzles are arranged in a matrix form consisting of orthogonal rows and columns, straight transfer pathways are appropriately arranged to intersect with each other at right angles. If the reaction container is movably provided, the reaction container is provided in a movable manner between the transfer pathway of the flow channel and the transfer pathway of the distal end of the processing nozzle.

If the reagent etc. storage unit and the dispenser device are provided as the reagent etc. feeder, the transfer pathway of the flow channel corresponds to the transfer pathway of the dispensing nozzle, and the transfer pathway is provided with the reagent etc. storage unit and the reaction container.

A fourth aspect of this invention is a magnetic particle parallel processing apparatus permitting repeated use of a container, wherein the reaction container and the liquid disposal tank are movably provided with respect to the distal end of the processing nozzle, and the reaction container is capable of passing through a feeding position on the transfer pathway of the distal end of the flow channel.

A fifth aspect of this invention is a magnetic particle parallel processing apparatus permitting repeated use of a container, wherein the reaction container and the liquid disposal tank are provided in a processing carriage capable of reciprocating movement along a straight line with respect to the distal end of the processing nozzle.

A sixth aspect of this invention is a magnetic particle parallel processing apparatus permitting repeated use of a container, wherein the reaction container is movably provided between a processing position on a transfer pathway of the distal end of the processing nozzle and a feeding position on a transfer pathway of the distal end of the flow channel.

Here, the term "processing position" means a position where magnetic particles in the reaction container are processed, and the term "feeding position" means a position where a reagent or other substance is fed to inside the reaction container. The processing position and the feeding position are determined depending on; the position or the transfer pathway of the distal end of the processing nozzle, and the position or the transfer pathway of the distal end of the flow channel of the reagent etc. feeder, respectively according to the processing content.

A seventh aspect of this invention is a magnetic particle parallel processing apparatus permitting repeated use of a container, wherein an inside bottom of the reaction container is formed so that a liquid can be sucked and discharged even though the distal end of the processing nozzle abuts thereon.

An eighth aspect of this invention is a magnetic particle parallel processing apparatus permitting repeated use of a container, wherein a gap portion having a width narrower than an aperture diameter of the distal end, and a length longer than the aperture diameter of the distal end, is formed in a vicinity of the center of the inside bottom of the reaction container.

Regarding the shape of the gap portion, for example, the horizontal cross-section of the inside bottom may be formed to have an elliptical hole whose minor axis is shorter than the aperture diameter and whose major axis is longer than the aperture diameter. In addition, an uniform downwardly inclined sloping face may also be formed from the wall of the container to the edge of the gap portion.

A ninth aspect of this invention is a magnetic particle parallel processing apparatus permitting repeated use of a container, wherein a water absorbent portion is provided in a rim of the opening of the liquid disposal tank.

Here, the "water absorbent portion" is made of a material having a water absorption property such as a sponge, a porous material, or an infiltrating material.

A tenth aspect of this invention is a method of magnetic particle parallel processing permitting repeated use of a container comprising: a suspension storing step for storing a first liquid obtained by feeding a magnetic particle suspension to at least one reaction container; a whole amount suction step for sucking the whole amount of the first liquid stored in the reaction container by inserting at least one distal end of a magnetic separator which has at least one processing nozzle with the distal end for sucking and discharging a liquid through the distal end, and which also has a magnetic means capable of applying a magnetic field to the interior of the distal end, into the reaction container; a whole amount discharging/feeding step for discharging the whole amount of the residual first liquid from the distal end into a liquid disposal tank in a state where the magnetic particles are attracted to the inner wall of the distal end of the processing nozzle by applying a magnetic field to the distal end, and for feeding a second liquid into the reaction container in parallel with the discharging operation; and a magnetic particle contacting step for contacting the magnetic particles with the second liquid by inserting the distal end of the processing nozzle into the reaction container and sucking the second liquid.

Here, the "first liquid" at least contains magnetic particles. In addition, for example, a specimen which contains a possibly bindable substance for a binding substance of the magnetic particle, and a reagent or other substance, are mixed therein. The term "whole amount" means approximately one hundred percent of the target amount. A negligible amount of this liquid within an extent of measurement error for the processing content to be applied may remain.

An eleventh aspect of this invention is a method of magnetic particle parallel processing permitting repeated use of a container, wherein in the contacting step the magnetic particles are contacted with the second liquid by re-suspending the magnetic particles in the second liquid in a state where the magnetic field is cancelled, or by sucking/discharging the second liquid while the magnetic particles are being attracted in a state where the magnetic field is applied.

A twelfth aspect of this invention is a method of magnetic particle parallel processing permitting repeated use of a container, wherein the first liquid containing the magnetic particle suspension or the second liquid is discharged from the reagent etc. storage unit which stores solutions constituting the first liquid and the second liquid, and the magnetic particle suspension, through a distal end of at least one flow channel of the reagent etc. feeder, by inserting the distal end of the flow channel into the reaction container at once.

For example, in a case where the reagent etc. feeder comprises a dispenser device and a reagent etc. storage unit, feeding of the first liquid containing the magnetic particle suspension or the second liquid is performed by inserting at once the distal end of at least one dispensing nozzle of the dispenser device which at least sucks and discharges a liquid, and dispensing from the reagent etc. storage unit which stores a solution component constituting the first liquid, and a solution component constituting the second liquid.

Here, the "first liquid" and the "second liquid" are made of at least one solution selected from the group consisting of various reagent solutions, a washing liquid, a specimen solution, and a magnetic particle suspension.

A thirteenth aspect of this invention is a method of magnetic particle parallel processing permitting repeated use of a container, wherein the first liquid in the whole amount suction step is replaced with the second liquid, the first liquid in the whole amount discharging/feeding step is replaced with the second liquid, and the second liquid in the whole amount discharging/feeding step and in the magnetic particle contacting step is replaced with a third liquid.

Here, the "third liquid" and other liquids to be used thereafter are also made of at least one solution selected from the group consisting of various reagent solutions, a washing liquid, a specimen solution, and a magnetic particle suspension.

A fourteenth aspect of this invention is a method of magnetic particle parallel processing permitting repeated use of a container, wherein an inside bottom of the reaction container is formed so that a liquid can be sucked and discharged even though the distal end abuts thereon, and the whole amount suction step is performed by sucking in a state where the distal end is abutted on the inside bottom of the reaction container.

A fifteenth aspect of this invention is a method of magnetic particle parallel processing permitting repeated use of a container, wherein the suspension storing step, the whole amount discharging/feeding step, and the whole amount suction step are performed by relatively moving the distal end of the flow channel with respect to the reaction container, and by relatively moving the reaction container and the liquid disposal tank with respect to the distal end of the processing nozzle.

A sixteenth aspect of this invention is a method of magnetic particle parallel processing permitting repeated use of a container, wherein the suspension storing step, the whole amount discharging/feeding step, and the whole amount suction step are performed by moving the reaction container between a processing position on a transfer pathway of the distal end of the processing nozzle and a feeding position on a transfer pathway of the distal end of the flow channel.

A seventeenth aspect of this invention is a method of magnetic particle parallel processing permitting repeated use of a container, wherein the suspension storing step, the whole amount discharging/feeding step, and the whole amount suction step are performed by moving the distal end of the flow channel with respect to the reaction container, and by moving the reaction container and the liquid disposal tank with respect to the distal end of the processing nozzle.

[Effects of the Invention]

According to the first aspect or the tenth aspect, processing for newly feeding a liquid to the reaction container for use in the processing of magnetic particles by each step according to the processing content, and removing the whole amount of the liquid, is repeated. Moreover, while the residual liquid is being disposed into the liquid disposal tank with the magnetic particles attracted to the inner wall of the distal end of the processing nozzle, the liquid for use in the next step is fed to the reaction container to shift to the next processing step. Accordingly, the same container can be repeatedly used irrespective of the number of steps. Thus, there is no need of increasing the number of containers for used in processing, irrespective of the incremental number of steps, and the working area can be saved. In addition, the liquid for use in the next step is fed to the reaction container during a given timing for when the residual liquid is disposed from the processing nozzle on completion of each step. As a result, the time for previously dispensing the liquid for use in each processing step can be saved so that magnetic particles can be quickly processed.

The suspended state of the magnetic particles required for processing in the liquid can be achieved by the sucking and discharging operation with use of the processing nozzle. Therefore, the magnetic particles can be reliably sucked in the suspended state, and removed from the reaction container. In addition, since the agitation operation for suspending the magnetic particles is not necessary during processing, cross-contamination due to liquid splashing can be reliably prevented.

According to the second aspect or the twelfth aspect, the distal end of the flow channel of the reagent etc. feeder is relatively movably provided with respect to the reaction container, and the liquid required for processing is fed by inserting its distal end into the reaction container. Accordingly, the liquid can be fed by inserting the distal end into the reaction container only when feeding is needed. Therefore, the distal end of the reagent etc. feeder and the distal end of the processing nozzle will not conflict with each other in the reaction container. Hence the feeding and the processing can be smoothly performed, and cross-contamination due to these distal ends touching each other can be avoided. In particular, when the reagent etc. storage unit and the dispenser device are used as the reagent etc. feeder, the assembling operation can be readily done using common parts for the apparatus used in the processing nozzle. Therefore the production cost can be saved.

According to the third aspect, the distal ends of the flow channel and the processing nozzle are made movable, and the reaction container is provided to exist on both of the transfer pathway of the distal end of the flow channel and the transfer pathway of the distal end of the processing nozzle. By so doing, the reaction container can be formed in a fixed state, or on a shortest pathway through which the container can pass any point of the transfer pathways.

According to the fourth aspect, the reaction container and the liquid disposal tank are movably provided with respect to the distal end of the processing nozzle, whereby the momentum can be reduced as compared to the case where the distal end of the processing nozzle is moved, and the apparatus structure and the movement control can be simplified by unitedly moving the reaction container and the liquid disposal tank.

According to the fifth aspect, the reaction container and the liquid disposal tank are provided in the processing carriage and subjected to reciprocating movement along a straight line with respect to the distal end of the processing nozzle, whereby the apparatus structure and the movement control can be further simplified.

According to the sixth aspect, the reaction container is movably provided between the processing position on the transfer pathway of the distal end of the processing nozzle and the feeding position on the transfer pathway of the distal end of the flow channel. Accordingly, by providing the feeding position and the processing position respectively at a point leading to a shortest distance between the transfer pathway of the distal end of the processing nozzle and the transfer pathway of the distal end of the flow channel, the movement distance of the reaction container can be shortened to thereby accelerate the processing. In addition, by providing the transfer pathway of the distal end of the processing nozzle and the transfer pathway of the distal end of the flow channel in a totally separate manner, for example, a parallel and adjacent arrangement, then collision between the processing nozzle and the flow channel can be prevented.

According to the seventh aspect, the eighth aspect, or the fourteenth aspect, the inside bottom of the reaction container is formed so that a liquid can be sucked and discharged even though the point of the distal end of the dispensing nozzle abuts on the inside bottom. Therefore, the whole amount of the contained liquid can be reliably sucked by abutting the distal end of the processing nozzle on the inside bottom. Accordingly, highly precise and reliable control can be performed by reliably sucking the whole amount of the liquid and the magnetic particles in the reaction container.

According to the ninth aspect, the whole amount of the residual liquid in the distal end can be reliably removed by providing the water absorbent portion.

According to the eleventh aspect, since the magnetic particles can be contacted with the liquid while being re-suspended, or while being attracted to the inner wall, various processings can be performed by selection according to the processing content. For example, in order to capture the target substance on the magnetic particles, the magnetic particles are re-suspended so as to increase the encounter probability between the magnetic particles and the target substance. Moreover, in order to wash the magnetic particles, the magnetic particles are contacted with a washing liquid while being attracted. By so doing, the dissociation of the captured target substance from the magnetic particles can be minimized.

According to the thirteenth aspect, an unlimited increase in the number of containers to be used can be prevented by repeatedly using the same reaction container irrespective of the incremental number of steps.

According to the fifteenth aspect, the sixteenth aspect, or the seventeenth aspect, the distal ends of the flow channel and the processing nozzle are relatively movably provided with respect to the reaction container, and the liquid disposal tank is relatively movably provided only with respect to the distal end of the processing nozzle. Therefore, the arrangement or control can be performed so as to increase the working efficiency according to the size of each device and the processing content.

BEST MODE FOR CARRYING OUT THE INVENTION

Next is a description of a magnetic particle parallel processing apparatus 10 permitting repeated use of a container according to a first embodiment of the present invention, with reference to FIG. 1 through FIG. 7.

As shown in FIG. 1, the magnetic particle parallel processing apparatus 10 permitting repeated use of a container comprises: a processing carriage 11 having at least a reaction container 12 for storing a liquid to be used, and a liquid disposal tank 14 capable of storing a liquid to be disposed; a reagent etc. feeder 16 with at least one flow channel for feeding at least two types of liquids selected from the group consisting of two or more types of solutions and a magnetic particle suspension according to the processing content, at a given amount and at a given timing, to the reaction container 12; and a magnetic separator 18 for sucking the liquid from the reaction container 12 and discharging the liquid into the disposal tank 14, as well as applying a magnetic field to the sucked liquid to thereby separate magnetic particles contained in the liquid, and canceling the magnetic field to thereby re-suspend and discharge the magnetic particles in a liquid. The distance between the reaction container 12 and the liquid disposal tank 14 in the processing carriage 11 is set equal to the distance between the processing position and the feeding position.

The whole of the magnetic particle parallel processing apparatus 10 permitting repeated use of a container is provided on, for example, a stage of about 600 mm length×500 mm width, and is housed in, for example, a case (not shown). The processing carriage 11 is movable with respect to the case or the stage within the case, and has a straight transfer pathway along the Y axis direction in the drawing which passes through under the transfer pathway of the magnetic separator 18 attached to the case and the transfer pathway of a dispensing nozzle head 17 that will be described later.

The reaction container 12 provided on the substrate 26 of the processing carriage 11 comprises two or more (eight in this example) deep wells 13 which are arrayed on a line along the X axis direction in the drawing at a given pitch. Below the substrate 26 of the reaction container 12 is provided a temperature controller 21 which controls the temperature with a Peltier element or the like, for heating or cooling the reaction container 12.

As shown in detail in FIG. 3 and FIG. 4, the liquid disposal tank 14 is provided inserted into a liquid disposal tank insertion hole 106 provided in the substrate 26 of the processing carriage 11. A water absorbent pad 102 serving as the water absorbent portion, in which two or more (eight in this example) disposal through holes 104 arrayed on two lines along the X axis direction in the drawing at the aforementioned pitch are provided, is supportedly provided on a step of a pad support 105 of an upper part of the liquid disposal tank 14. The water absorbent pad 102 is made of a material having a water absorption property such as a sponge or a porous member.

Returning back to FIG. 1, the processing carriage 11 also has, in addition to the reaction container 12 and the liquid disposal tank 14: a specimen container 20 comprising two or more (eight in this example) deep wells 13 arrayed on a line along the X axis direction in the drawing at the aforementioned pitch, and capable of containing a specimen; a container 24 comprising two or more (eight in this example) deep wells arrayed on a line along the X axis direction in the drawing at the aforementioned pitch, and capable of storing a PCR solution or a dissociation solution; and a tip rack 22 for storing, at the aforementioned pitch, two or more (eight in this example) dispensing tips 48 which are attachable to the processing nozzles 50, serving as the distal ends of the processing nozzles 50 of the magnetic separator 18 that will be described later.

The reagent etc. feeder 16 has: a reagent etc. storage unit 19 which stores various solutions and a magnetic particle suspension required for processing; and a dispensing nozzle head 17 which has a dispensing tip 38 that is insertable into each well 13 of the reaction container 12, and is capable of sucking various solutions and a magnetic particle suspension from the reagent etc. storage unit 19, and of transferring and discharging the same into respective wells 13 of the reaction container 12, through the dispensing tip 38.

The reagent etc. storage unit 19 is movable with respect to the case within the case, and is provided in a feeding carriage 30 having a straight transfer pathway along the Y axis direction in the drawing which passes through under the transfer pathway of the dispensing nozzle head 17.

In the substrate of the feeding carriage 30 are provided two or more (six in this example) reagent etc. storage containers 28, a magnetic particle suspension storage container 32 for storing a magnetic particle suspension, and two or more (seven in this example) holes 34 for storing the single purpose dispensing tips 38 for each of the reagent etc. storage containers 28 and the magnetic particle suspension storage container 32.

In addition, regarding the magnetic particle suspension storage container 32, in order to suspend the stored magnetic particles in the liquid, the magnetic particle suspension storage container 32 is provided with an agitation mechanism for suspending the stored magnetic particles in the liquid. The agitation mechanism is achieved by inwardly denting the container to provide an internal projection, and latching the outer dent with a projection of an external rotation mechanism, so as to link the container with the rotation mechanism, followed by rotation about the rotation axis along the central axis of the container. A motor serving as the rotation mechanism, is stored in a motor case 35.

The dispensing nozzle head 17 has a dispensing nozzle 41 serving as the flow channel fitted with a dispensing tip 38 serving as the distal end that is insertable into the reagent etc. storage containers 28, the magnetic particle suspension storage container 32, and the respective wells 13 of the reaction container 12. The bottom end of the dispensing nozzle 41 is tightly attachable to the opening on the top end of the dispensing tip 38. The top end of the dispensing nozzle 41 is communicated with a cylinder 40 to be capable of sucking and discharging. The cylinder 40 is attached to a Z axis movable body 42 which is movable in the Z axis direction. The Z axis movable body 42 is provided in a movable manner in the Z axis direction, on the side face of a base 36 of the nozzle head. In addition, the base 36 is provided in a movable manner in the X axis direction along a guide rail 44 that is provided to cross over above the respective transfer pathways of the feeding carriage 30 and the processing carriage 11 projected onto the stage. Moreover, at the bottom of the base 36 is provided a tip detachment member 39 that is formed in a U-shape with two projections having a gap smaller than the diameter of the opening of the dispensing tip 38 but greater than the diameter of the dispensing nozzle 41, in an advanceable/retreatable manner with respect to the dispensing tip 38.

The magnetic separator 18 has: two or more (eight in this example) dispensing tips 48 as the distal end insertable into the reaction container 12 and the liquid disposal tank 14; eight processing nozzles 50 arrayed on a line (along the X axis direction in the drawing) at the aforementioned pitch and fitted with the dispensing tips 48 at the distal ends thereof, for sucking and discharging liquids through the dispensing tips 48; and a magnet support 74 serving as the magnetic means capable of applying a magnetic field to the respective dispensing tips 48 to thereby attract magnetic particles contained in the liquid inside the dispensing tips 48 to the inner walls thereof to effect separation of the magnetic particles, and canceling the magnetic field to thereby release the attracted magnetic particles and re-suspend the same in a liquid.

On the transfer pathway of the processing carriage 11 are located; a processing position which is an intersection point with the Z axis passing through the dispensing tip 48, and a feeding position (not always fixed) which is an intersection point with the transfer pathway of the dispensing tip 38 serving as the distal end of the flow channel.

Above the processing nozzles 50 of the magnetic separator 18 are provided a cylinder container 52 for storing two or more (eight in this example) cylinders (not shown) that are communicated with the respective processing nozzles, a cylinder support member 51 for supporting the cylinders, two or more (eight in this example) rods 54 for driving plungers which slide inside the cylinders, a drive plate 56 linked with the two or more rods 54 to effect vertical movement thereof at once, a nut portion 61 provided on the drive plate 56, a ball screw 60 screwed in the nut portion 61, a sucking/discharging motor 70 for rotationally driving the ball screw 60, and a nozzle support movable portion 58 which supports the sucking/discharging motor 70 and is provided in a vertically movable manner through the guidance of a guide pole 57.

The guide pole 57 is provided on the Z axis movable body 64. The Z axis movable body 64 is driven by; a rotatable roller 69 which is rotated by the rotational drive of a motor 71 attached to a base 66 that is fixed to the case (not shown), a belt 67 which transmits the rotation of the rotatable roller 69, a ball screw (not shown) which is rotationally driven by a rotatable roller 68 around which is wrapped the belt 67, and a nut portion (not shown) which is screwed on the ball screw and provided on the nozzle support movable portion 58. The nozzle support movable portion 58 is merely mounted on the Z axis movable body 64 by its own weight while being restricted by the guide pole 57, and thus is vertically moved with the Z axis movable body 64. However, when the distal ends of the dispensing tips 48 attached to the processing nozzles 50 abut on the inside bottom of the containers (bottom landing), the reactive force received at this time makes the nozzle support movable portion 58 move upward through the guidance of the guide pole 57. The bottom landing can be detected by detecting the movement of the nozzle support movable portion 58 with a separately provided optical sensor (not shown). The optical sensor corresponds to the bottom landing detector. In FIG. 1, reference symbol 55 denotes a head provided on the top end of the rod 54 for linking the rod 54 to the drive plate 56.

Below the cylinder support member 51, a cylinder container 52 which stores cylinders (not shown) inside, is provided in a relatively movable manner with respect to the cylinders, and has an internal width slightly smaller than the diameter of the top end of the dispensing tips 48 attached to the processing nozzles 50. The cylinder container 52 is pushed down by a pin 53 projecting downward from the drive plate 56 when the drive plate 56 is lowered deeper than a certain depth, to thereby detach the pipetting tips 48 from the processing nozzles 50.

At the bottom of the magnetic separator 18 is provided a bottom portion 78 fixed to the base 66. A magnet support 74 for applying a magnetic field to the interior of the dispensing tips 48 as the distal end, is provided on the bottom portion 78 in an advanceable/retreatable manner with respect to the axes of the dispensing tips 48 along the Y axis direction. Moreover, slightly above the magnet support 74, a dripping prevention plate 76 for preventing liquid dripping from the dispensing tips 48, is provided in an advanceable/retreatable manner along the Y axis direction, so as to cover below the dispensing tips 48.

In FIG. 2, reference symbol 80 denotes a motor for driving the magnet support 74 and the dripping prevention plate 76. In addition, reference symbol 86 denotes an aperture of the dispensing tip 48.

In FIG. 3, reference symbol 100 denotes a magnet. On the magnet support 74 are arranged two or more (eight in this example) magnets 100 on a line along the X axis direction at the aforementioned pitch, which are provided to be approachable to the respective dispensing tips 48.

FIG. 5 shows a dispensing tip 48 and a well 13 that have been withdrawn from the reaction container 12.

As shown in FIG. 5(b), the dispensing tip 48 comprises a small diameter portion 88 having at its distal end an aperture 86 that is capable of inflow and outflow of a fluid, a large diameter portion 92 having an opening 94 that is tightly attachable to the distal end of the processing nozzle 50, and a transitional portion 90 between the small diameter portion 88 and the large diameter portion 92. The magnet 100 of the magnet support 74 is preferably closer to the exterior wall of the small diameter portion 88.

As shown in FIGS. 5(f) and (g), the inside bottom 84 of the well 13 into which the dispensing tip 48 can be inserted, is in an elliptical shape whose major axis is longer than the outer diameter of the distal end of the dispensing tip 48 and whose minor axis is shorter than the outer diameter of the distal end of the dispensing tip 48. In addition, a uniform downwardly inclined sloping face is formed from the wall of the container to the edge of the elliptical inside bottom 84 which corresponds to a gap portion 85. Therefore, the whole amount of a liquid can be sucked and discharged even though the distal end of the dispensing tip 48 abuts on the inside bottom 84.

Next is a description of the operation of the magnetic particle parallel processing apparatus 10 permitting repeated use of a container according to the first embodiment, with reference to FIG. 6 and FIG. 7.

In FIG. 6, the processing carriage 11 is moved until the tip rack 22 comes to the processing position, and then the processing nozzles 50 are lowered to tightly insert the distal ends of the processing nozzles 50 into the openings of the dispensing tips 48 stored in the tip rack 22 to thereby attach them. Next, the processing nozzles 50 are elevated while the processing carriage 11 is moved until the specimen container 20 comes to the processing position. Then, the dispensing tips 48 are lowered to insert them into the respective wells of the specimen container 20. After a given amount of each specimen has been sucked, the dispensing tips 48 are elevated. Next, the processing carriage 11 is moved until the reaction container 12 comes to the processing position. Then the dispensing tips 48 are lowered to insert the distal ends thereof into the respective wells 13, and the whole amount of the sucked specimen is discharged into each well 13.

Next, the processing carriage 11 is moved until the reaction container 12 comes to the first feeding position where the transfer pathway of the processing carriage 11 and the transfer pathway of the dispensing nozzle head 17 intersect on the stage, and the feeding carriage 30 is moved to locate the reagent etc. storage container 28a on the transfer pathway of the dispensing nozzle head 17. Then, the distal end of the dispensing nozzle 41 of the dispensing nozzle head 17 is inserted into the opening of the dispensing tip 38 stored in the hole 34, and the Z axis movable body 42 is moved downward to thereby tightly attach the dispensing tip 38 to the dispensing nozzle 41. The dispensing tip 38 is elevated and then moved along the guide rail 44. Then, the dispensing tip 38 is lowered into the reagent etc. storage container 28a to suck a given amount of the first reagent, and is then elevated and moved along the guide rail 44. The dispensing tip 38 is lowered to insert it into each well 13 of the reaction container 12 to discharge the reagent, and is then elevated and moved to the next well 13. In such a manner, a given amount is serially dispensed.

Next, the dispensing tip 38 is detached in the hole 34 by elevating the dispensing nozzle 41 in a state where the tip detachment member 39 is latched with the dispensing nozzle 41 in a position slightly above the top end of the dispensing tip 38. Then, the dispensing tip 38 is moved to a reagent etc. storage container 28b next to a reagent etc. storage container 28a in a state where the reaction container 12 is left in the same feeding position. A single purpose dispensing tip 38 is attached to the distal end of the dispensing nozzle 41 of the dispensing nozzle head 17 in the same manner to suck a second reagent, and is then moved along the guide rail 44. By so doing, a given amount is serially dispensed into each well 13 of the reaction container 12.

Next, the dispensing tip 38 is detached in the hole 34, and then the feeding carriage 30 is moved until the magnetic particle suspension storage container 32 comes to the transfer pathway of the dispensing nozzle head 17. A single purpose dispensing tip 38 is attached to the distal end of the dispensing nozzle 41 of the dispensing nozzle head 17 to suck the magnetic particle suspension, and is then moved along the guide rail 44. In such a manner, a given amount of the magnetic particle suspension is serially fed to each well 13 of the reaction container 12. After the feeding operation, the dispensing tip 38 is detached in the hole 34 by using the tip detachment member 39. The magnetic particle is, for example, magnetized cellulose, or a magnetic particle having a bindable substance such as an antibody which is chemically bound to a functional group on the surface. The aforementioned process corresponds to the suspension storing step, and the liquid stored in the reaction container 12 corresponds to the first liquid.

Next, as shown in FIG. 7, the processing carriage 11 is moved until the reaction container 12 is located in the processing position, and the dispensing tips 48 of the magnetic separator 18 are lowered to insert the distal ends thereof into the respective wells 13 of the reaction container 12. When the bottom landing on the inside bottom has been detected by the bottom landing detector, a bottom landing signal is output to stop lowering the dispensing tips 48. Then, in a state where the distal ends of the dispensing tips 48 abut on the inside bottom, the magnetic particle suspension stored in the reaction container 12 is agitated through repetitive sucking and discharging to thereby enhance the encounter probability between the surface of the magnetic particles and the target substance in the specimen.

At this time, incubation is performed to effect reaction bonding processing by retaining the interior of the reaction container 12 at a given constant temperature through the control of the temperature controller provided below the reaction container 12. Then, the dispensing tips 48 are inserted and lowered into the reaction container 12. When the bottom landing on the inside bottom has been detected by the bottom landing detector, a bottom landing signal is output to stop lowering the dispensing tips 48. Then, in a state where the distal ends of the dispensing tips 48 abut on the inside bottom, the sucking operation is started to suck the whole amount of the liquid contained in each well 13 of the reaction container 12 until the respective wells 13 of the reaction container 12 become empty. During or after the sucking operation, the magnet support 74 is brought closer to the small diameter portions 88 of the dispensing tips 48 to thereby apply a magnetic field to the interiors of the dispensing tips 48 so as to attract the magnetic particles capturing the target substance in the sucked liquid to the inner walls of the small diameter portions 88 to effect separation of the magnetic particles. The aforementioned process corresponds to the whole amount suction step.

Next, in a state where the magnetic particles are attracted to the inner walls and the liquids are contained inside, the dispensing tips 48 are elevated to withdraw from the reaction container 12. Then, as shown in FIG. 6, the processing carriage 11 is moved until the liquid disposal tank 14 is located in the processing position, that is, a position under the respective dispensing tips 48 of the magnetic separator 18. This brings the reaction container 12 in the processing carriage 11 to the transfer pathway of the dispensing tip 38, that is, the feeding position (the distance between the liquid disposal tank 14 and the reaction container 12 has been set equal to the distance between the processing position and the transfer pathway of the dispensing tip 38).

Here, the dispensing tips 48 are lowered to the position shown in FIG. 4 in a state where the magnet support 74 is brought closer to apply a magnetic field thereto. Then, the whole amount of the sucked liquid is discharged into the liquid disposal tank 14. Accordingly, only the magnetic particles attracted to the inner wall are separated and remain in the dispensing tip 48. The magnetic particles are meant to capture the target substance contained in the specimen.

When the sucked liquids in the dispensing tips 48 are being discharged into the liquid disposal tank 14, as described before, reagents required for processing the target substance, a washing liquid, and the like are dispensed into the empty respective wells 13 of the reaction container 12 by the dispensing tip 38 in the abovementioned manner. That is, the feeding carriage 30 is moved until the reagent etc. storage containers 28c and 28d storing the next reagent or other substance come to the transfer pathway of the dispensing tip 38, and dispensing is serially carried out in each well 13 of the reaction container 12. The aforementioned process corresponds to the whole amount discharging/feeding step, and the liquid stored in the reaction container corresponds to the second liquid.

On completion of the feeding operation by dispensing into the reaction container 12, as shown in FIG. 7, the processing carriage 11 is moved until the reaction container 12 storing a liquid corresponding to the second liquid comes to the processing position. Then, the dispensing tips 48 having the magnetic particles attracted to their inner walls are lowered to insert the distal ends thereof into the respective wells 13. When the bottom landing on the inside bottom has been detected by the bottom landing detector, the lowering operation of the dispensing tips 48 is stopped. Then, in a state where the distal ends of the dispensing tips 48 abut on the inside bottom, the second liquid stored in the reaction container 12 is agitated through repetitive sucking and discharging. In this case, the magnetic particles capturing the target substance on the surface may be suspended in a state where the magnetic field is cancelled, or may be suspended while being attracted to the inner wall. By so doing, the second liquid is brought into contact with the magnetic particles, and therefore the target substance and the second liquid are made to encounter or react with each other. The aforementioned process corresponds to the magnetic particle contacting step.

When the processing of the magnetic particles has been completed in the above manner, for example, the target substance is dissociated from the magnetic particles. Then for example, the dissociation container 24 is moved to the processing position to store the dissociated target substance. In this case, in order to prevent liquid dripping, the dripping prevention plate 76 is moved forward to under the dispensing tips 48 so that the dripping prevention plate 76 can cover the bottom side of the dispensing tips 48. If the processing of the magnetic particles proceeds further, the whole amount suction step, the whole amount discharging/feeding step, and the magnetic particle contacting step are further repeatedly performed. In this case, a third liquid or the like is fed instead of the second liquid.

FIG. 8 shows the magnetic particle parallel processing apparatus 110 permitting repeated use of a container according to a second embodiment. The magnetic particle parallel processing apparatus 110 permitting repeated use of a container comprises: a processing carriage 111 having a reaction container 112 capable of storing a liquid to be used with wells arrayed in a matrix form of 8 rows×12 columns, and a liquid disposal tank 114 capable of storing a liquid to be disposed; a reagent etc. feeder 116 with at least one (twelve in this example) flow channel for feeding at least two types of liquids selected from the group consisting of two or more types of solutions and a magnetic particle suspension according to the processing content, at a given amount and at a given timing, to the reaction container 112; and a magnetic separator 118 for sucking the liquid from the reaction container 112 and discharging the liquid into the disposal tank 114, as well as applying a magnetic field to the sucked liquid to thereby separate magnetic particles contained in the liquid, and canceling the magnetic field to thereby re-suspend and discharge the magnetic particles in a liquid. The distance between the reaction container 112 and the liquid disposal tank 114 in the processing carriage 111 is set equal to the distance between the processing position and the feeding position.

The whole of the magnetic particle parallel processing apparatus 110 permitting repeated use of a container is provided on, for example, a stage 132 of about 600 mm length× 900 mm width, and is enclosed in a case (not shown). The processing carriage 111 is movable with respect to the stage 132, and has a transfer pathway along the Y axis direction so as to intersect at right angles with the transfer pathway of the magnetic separator 118 which is movable along the X axis direction and the transfer pathway of a dispenser device 126 of the reagent etc. feeder 116 that will be described later, which is also movable along the X axis direction.

The reaction container 112 provided on the substrate 113 of the processing carriage 111 comprises two or more (96 in this example) deep wells 13 which are arrayed in a matrix form at a given pitch. Below the substrate 113 of the reaction container 112 is provided a temperature controller (not shown) which controls the temperature with a Peltier element or the like, for heating or cooling the reaction container 112. In the liquid disposal tank 114, an aperture is provided in the center and downwardly inclined sloping faces are provided at the periphery of the aperture.

In the processing carriage 111, the reaction container 112 and the liquid disposal tank 114 are provided at an interval having a pitch equal to the pitch between the transfer pathway of the dispenser device 126 and the transfer pathway of the magnetic separator 118 that will be described later. The reaction container 112 is movable along the Y axis direction between the transfer pathway of the dispenser device 126 and the transfer pathway of the magnetic separator 118. The position of the reaction container 112 in FIG. 8(a) is the feeding position, and the position of the reaction container 112 in FIG. 8(b) is the processing position.

The reagent etc. feeder 116 has: a reagent etc. storage unit 130 which stores various solutions and a magnetic particle suspension required for processing, in 12 rows×one or more columns; a tip rack 128 which stores dispensing tips 38 in 12 rows×3 columns; and a dispenser device 126 which has twelve dispensing tips 38 arrayed in the Y axis direction and insertable into the reagent etc. storage unit 130 and the respective wells 13 of the reaction container 112, and which is capable of sucking various solutions and a magnetic particle suspension from the reagent etc. storage unit 130 and of transferring and discharging the same into the respective wells 13 of the reaction container 112, through the dispensing tips 38.

The configuration of the dispenser device 126 is approximately the same as that of the abovementioned magnetic separator 18, except that the device 126 is movable on the stage 132 along the X axis direction, has twelve nozzles, and has no magnet support 74. Therefore detailed description thereof is omitted.

As shown in FIG. 9, the magnetic separator 118 has: two or more (96 tips arrayed in a matrix form of 8 rows×12 columns in this example) dispensing tips 134 serving as the distal end insertable into the reaction container 112 and the liquid disposal tank 114; 96 processing nozzles 136 arrayed in a matrix form at the aforementioned pitch and fitted with the dispensing tips 134 at the distal ends thereof, for sucking and discharging a liquid through the dispensing tips 134; and a magnet support 137 serving as the magnetic means capable of applying a magnetic field to the respective dispensing tips 134 to thereby attract magnetic particles contained in the liquid inside the dispensing tips 134 to the inner walls thereof to effect separation of the magnetic particles, and canceling the magnetic field to thereby release the attracted magnetic particles and re-suspend the same in a liquid.

Furthermore, in the magnetic separator 118, above the processing nozzles (not shown) are provided: two or more (96 cylinders in 8 rows×12 columns in this example) cylinders 138 that are communicated with the respective processing nozzles; two or more (96 rods in 8 rows×12 columns in this example) rods 140 for driving plungers which slide inside the cylinders; a drive plate 142 linked with the two or more rods 140 to effect vertical movement thereof at once; an actuator 144 linked with the drive plate 142 to effect vertical movement of the drive plate 142; a nut 146 linked with the actuator 144 and screwed on a ball screw 150 for vertically driving the actuator 144 so as to vertically and translationally move by the rotation of the ball screw 150; and the ball screw 150 which is rotatably driven by a sucking/discharging motor 152. What vertically supports the sucking/discharging motor 152 and the actuator 144 is a nozzle head support 148. The nozzle head support 148 is linked with a nut portion 160 that will be described later.

Below the cylinders 138 is provided a tip detaching plate 145 having holes with diameters greater than the diameter of the nozzle (not shown) and smaller than the top end of the dispensing tip 134, through which the nozzles are provided. The drive plate 142 is provided with a tip detaching pin 143 that is projected downward therefrom and can be contacted with the tip detaching plate 145. When the drive plate 142 is lowered deeper than the position of FIG. 9, the dispensing tips 134 being attached to the nozzles are detached from the nozzles by being wiped off.

The magnetic separator 118 further has a frame 154 which is movably supported in the X axis direction on the stage 132 by a transfer mechanism attached to the case. The frame 154 has; a ball screw 156 which is rotatably supported and extends in a vertical direction (Z axis direction), a nut portion 160 screwed on the ball screw 156 and linked with the nozzle head support 148 via a linker 158 for vertically and translationally moving the nozzle head support 148, and a Z axis motor 162 supported by the frame 154 for rotationally driving the ball screw 156. This apparatus also has, though not shown, a controller for controlling the magnetic separator 118, the dispenser device 126, the processing carriage 172, the feeding carriage, the temperature controller, and the like. The controller has, for example, an information processor comprising a CPU and a memory, a data input facility such as a mouse and a keyboard, a display device such as a liquid crystal panel, a data output facility such as a printer, a communication means, a driver for external memories such as CD and DVD, and the like (this also applies to the first embodiment).

At the bottom of the magnetic separator 118 is provided an under plate 157 fixed to the frame 154, and a magnet support 137 is movably provided through the guidance of a guide rail 153 along the Y axis direction for applying a magnetic field to the interior of the dispensing tips 134 as the distal end. The magnet support 137 is provided with five comb tooth members 141 projecting in a comb shape and extending in the Y axis direction to be insertable into spaces between 12 columns of the dispensing tips 134 by two columns in the array of the dispensing tips 134. On both sides of the five comb tooth members 141 are arrayed eight magnets 139 respectively so that a magnetic field can be applied to the interior of all 96 dispensing tips 134 when the members 141 enter into the spaces. In FIG. 9, reference symbol 155 denotes a motor for driving the magnet support 137.

FIG. 10 shows the magnetic particle parallel processing apparatus 170 permitting repeated use of a container according to a third embodiment, in which the same reference symbols are used for components the same as those in FIG. 8, and description thereof is omitted. The magnetic particle parallel processing apparatus 170 permitting repeated use of a container comprises: a processing carriage 172 having a reaction container 112 capable of storing a liquid to be used with wells arrayed in a matrix form of 8 rows×12 columns; a liquid disposal tank 114 capable of storing a liquid to be disposed; a reagent etc. feeder 116 with at least one (twelve in this example) flow channel for feeding at least two types of liquids selected from the group consisting of two or more types of solutions and a magnetic particle suspension according to the processing content, at a given amount and at a given timing, to the reaction container 112; and a magnetic separator 118 for sucking the liquid from the reaction container 112 and discharging the liquid into the disposal tank 114, as well as applying a magnetic field to the sucked liquid to thereby separate magnetic particles contained in the liquid, and canceling the magnetic field to thereby re-suspend and discharge the magnetic particles in a liquid.

The whole of the magnetic particle parallel processing apparatus 170 permitting repeated use of a container is provided on a stage 174. The processing carriage 172 is movable with respect to the stage 174 within the stage 174, and has a transfer pathway along the Y axis direction so as to intersect at right angles with the transfer pathway of the magnetic separator 118 which is movable along the X axis direction, and the transfer pathway of the dispenser device 126 of the reagent etc. feeder 116 that will be described later, which is also movable along the X axis direction.

The reaction container 112 provided on the substrate 173 of the processing carriage 172 comprises two or more (96 in this example) deep wells 13 arrayed in a matrix form at a given pitch. Below the substrate 173 of the reaction container 112 is provided a temperature controller (not shown) which controls the temperature with a Peltier element or the like, for heating or cooling the reaction container 112. Unlike the case of FIG. 8, the liquid disposal tank 114 is fixed to the transfer pathway of the magnetic separator 118. In the liquid disposal tank 114, an aperture is provided in the center, and downwardly inclined sloping faces are provided at the periphery of the aperture.

Because of the processing carriage 172, the reaction container 112 is movable along the Y axis direction between the transfer pathway of the dispenser device 126 and the transfer pathway of the magnetic separator 118. The position of the reaction container 112 in FIG. 10 (*a*) corresponds to the feeding position, and the position of the reaction container 112 in FIG. 10 (*b*) corresponds to the processing position.

The respective embodiments mentioned above are specifically described for better understanding of the present invention, and are not to be considered as limiting of any other embodiment. Accordingly, modifications can be made without departing from the scope of the invention. For example, in the aforementioned embodiments, the description was made for only the case where the number of the reaction containers was 8 or 96 (8 rows×12 columns). However, the number of the reaction containers is not to be limited to these cases, and can be one, ten, twelve, 384 (16 rows×24 columns), 1536 (32 rows×48 columns), or other various numbers.

In addition, the shape or the configuration of each reaction container, liquid disposal tank, magnetic separator, reagent etc. feeder, and the like are not to be limited to the aforementioned examples, and various shapes can be applied. In particular, regarding the reagent etc. feeder, the description was made only about the cases where the dispenser device and the dispensing nozzle head were used. However, for example, reagents may also be fed by a pump.

Moreover, the abovementioned components and devices such as the processing nozzle, the dispensing nozzle head, the dispensing tip, the reaction container, the liquid disposal tank, the magnetic separator, the bottom landing detector, the reagent etc. storage container, the water absorbent portion, the magnetic means, and the respective parts constituting them can be arbitrarily combined with appropriate modifications.

[Industrial Applicability]

The present invention relates to a magnetic particle parallel processing apparatus permitting repeated use of a container, and a method of magnetic particle parallel processing permitting repeated use of a container. The present invention relates to various fields which require handling of biopolymer or biological low molecular materials such as genes, immune systems, amino acids, proteins, and sugars, for example, industrial fields, agricultural fields such as food, agricultural production, and fishery processing, pharmaceutical fields, medical fields such as sanitation, health, immunization, diseases, and genetics, scientific fields such as chemistry and biology, and the like. The present invention is an effective method particularly for continuously performing a series of processings using a large number of reagents and substances in a given order.

Figure 1:
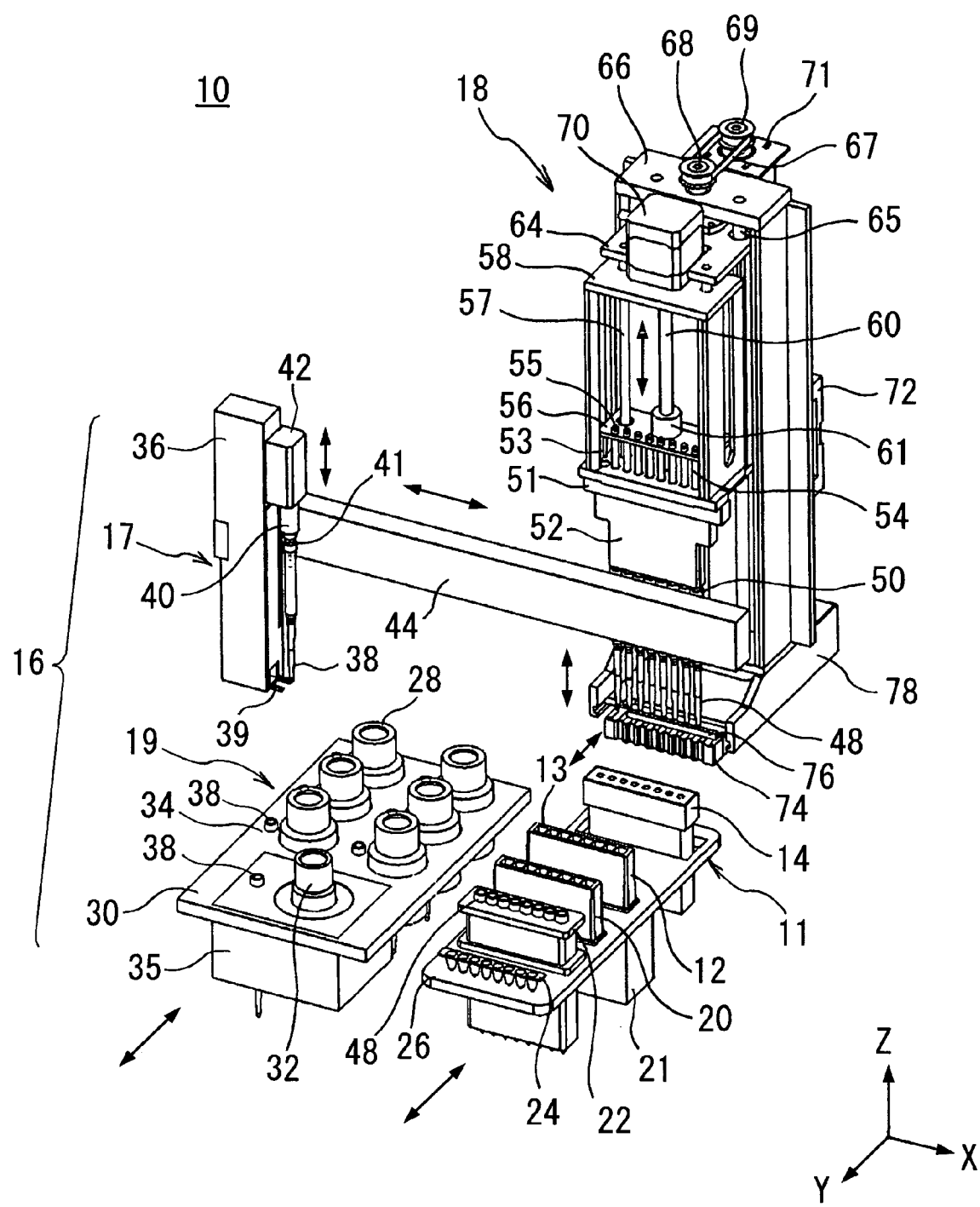
FIG. 1 is a perspective view of a magnetic particle parallel processing apparatus permitting repeated use of a container according to a first embodiment of the present invention.
Figure 2:
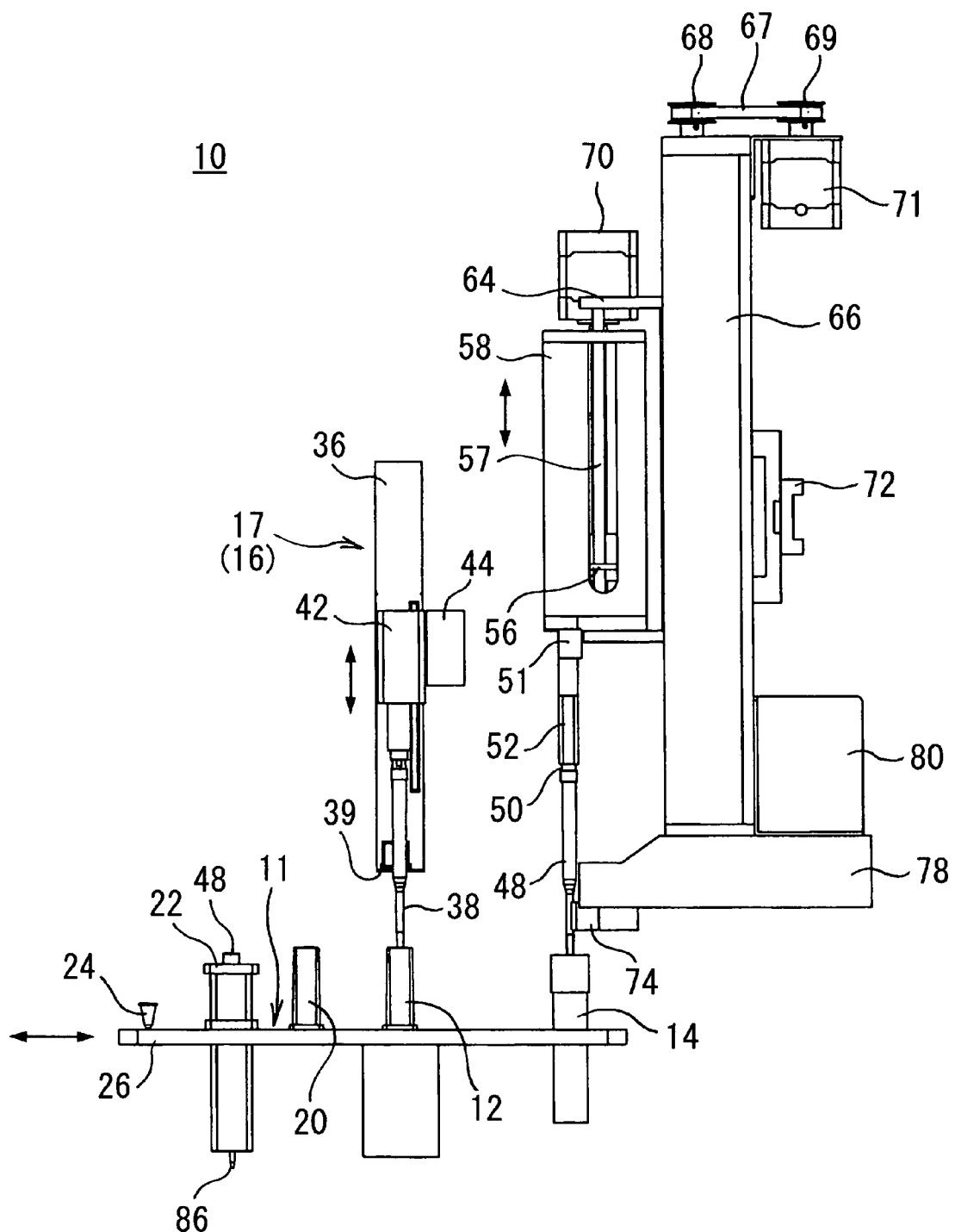
FIG. 2 is a side view of the magnetic particle parallel processing apparatus permitting repeated use of a container according to the first embodiment of the present invention.
Figure 3:
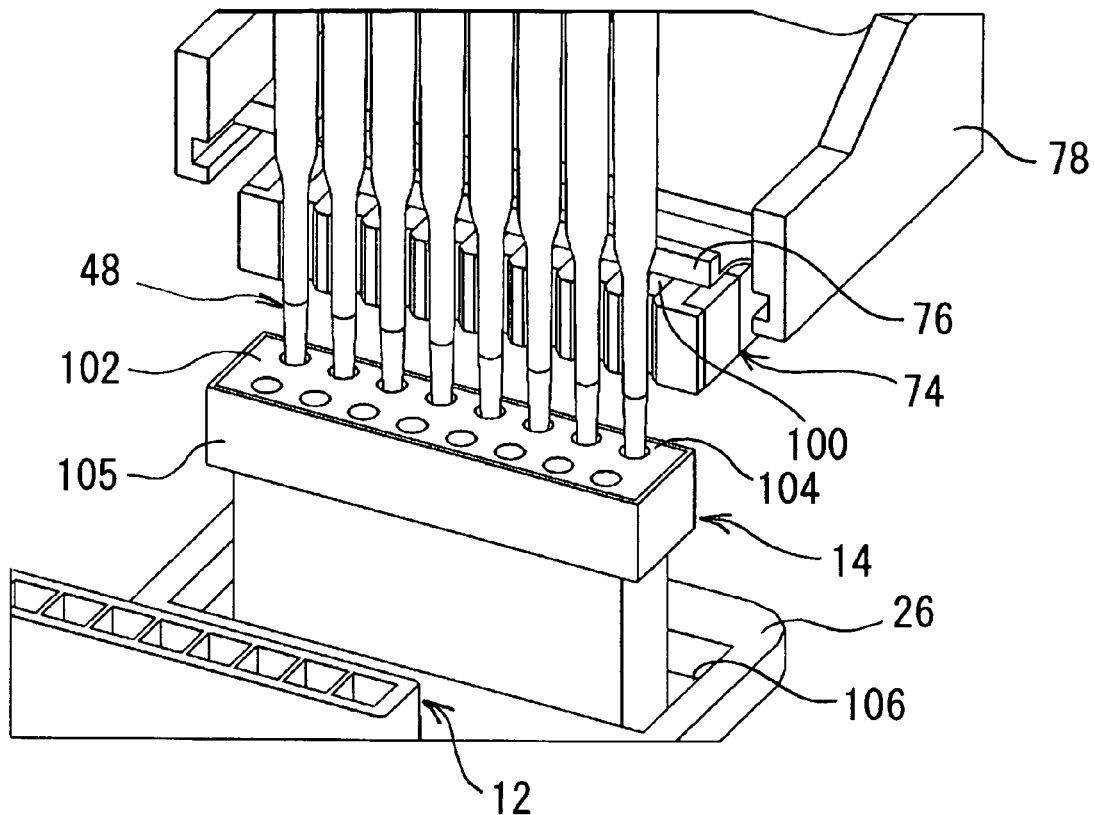
FIG. 3 is a perspective view for explaining the operation of the magnetic particle parallel processing apparatus permitting repeated use of a container according to the first embodiment of the present invention.
Figure 4:
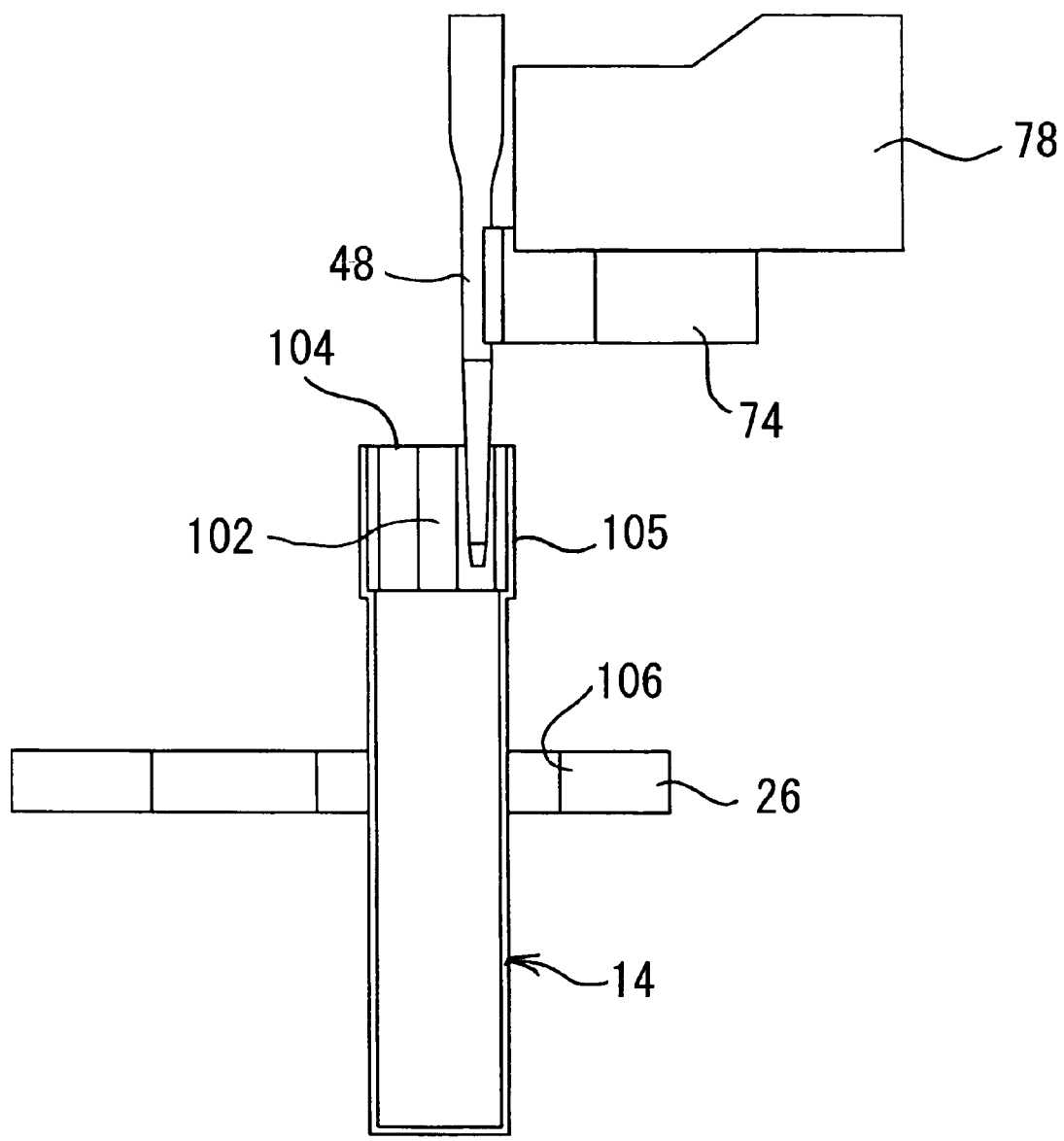
FIG. 4 is a side view for explaining the operation of the magnetic particle parallel processing apparatus permitting repeated use of a container according to the first embodiment of the present invention.
Figure 5:
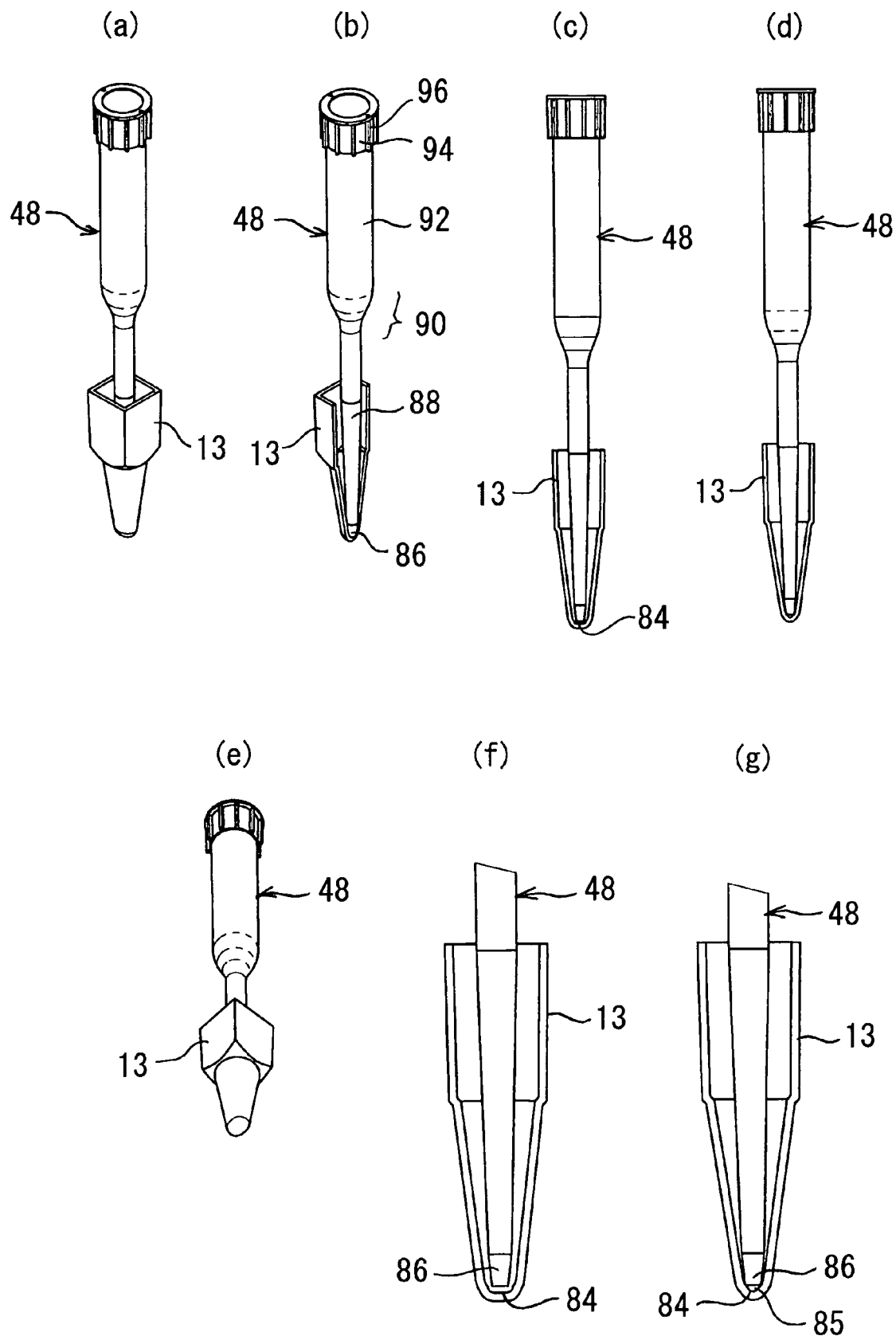
FIG. 5 is an explanatory diagram of the reaction container according to the first embodiment of the present invention.
Figure 6:
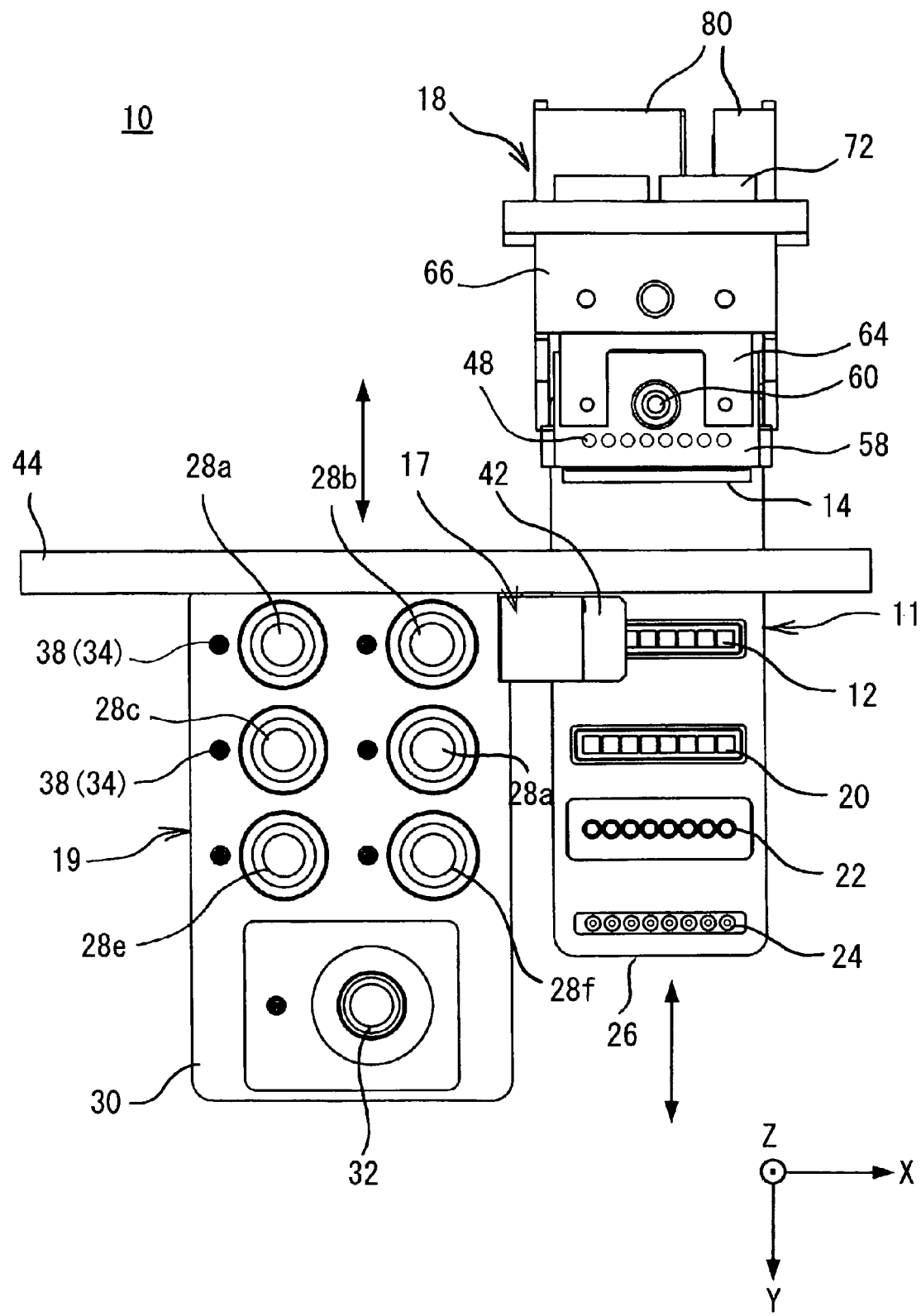
FIG. 6 is a plan view for explaining the operation of the magnetic particle parallel processing apparatus permitting repeated use of a container according to the first embodiment of the present invention.
Figure 7:
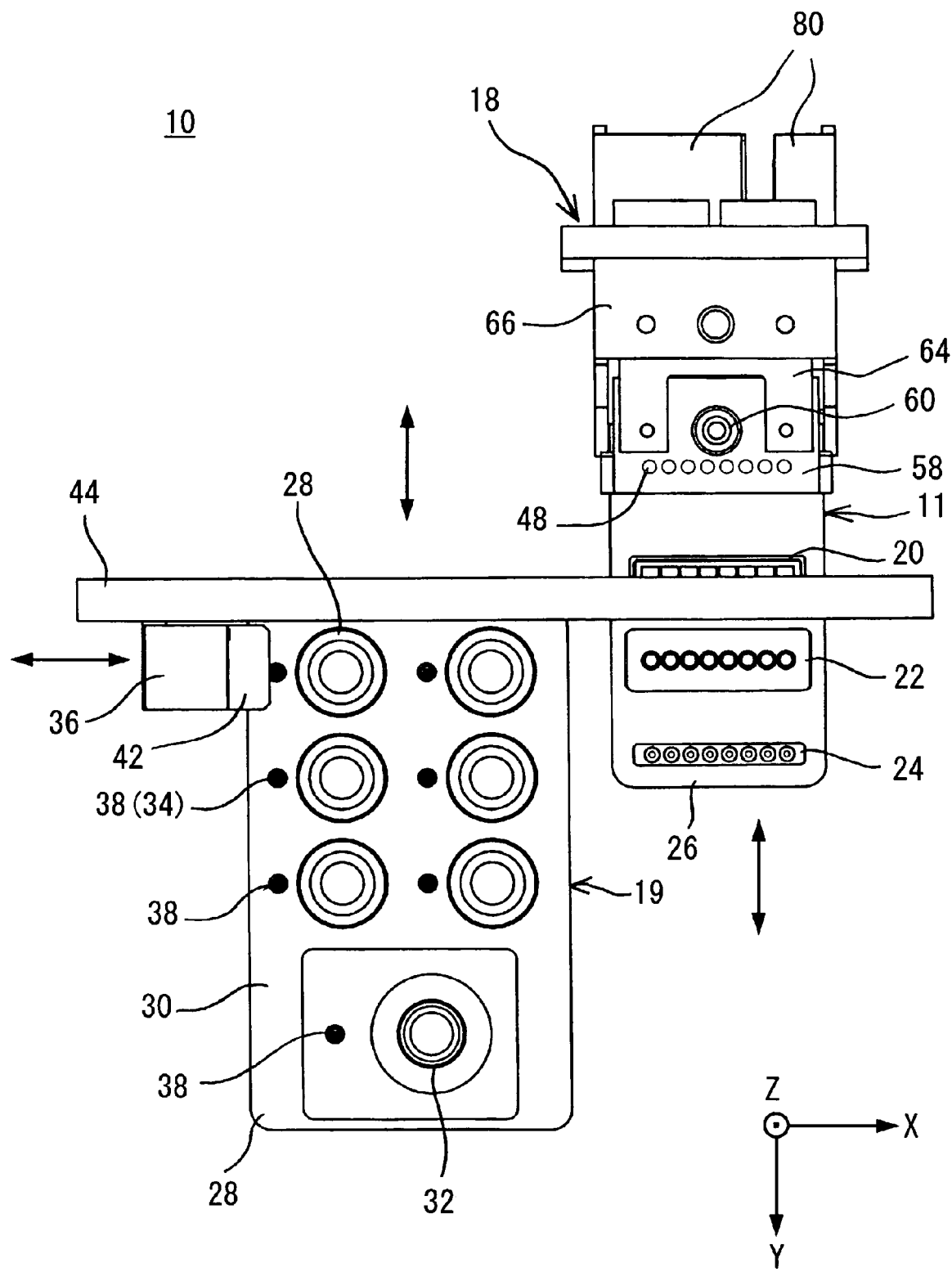
FIG. 7 is a plan view for explaining the operation of the magnetic particle parallel processing apparatus permitting repeated use of a container according to the first embodiment of the present invention.
Figure 8:
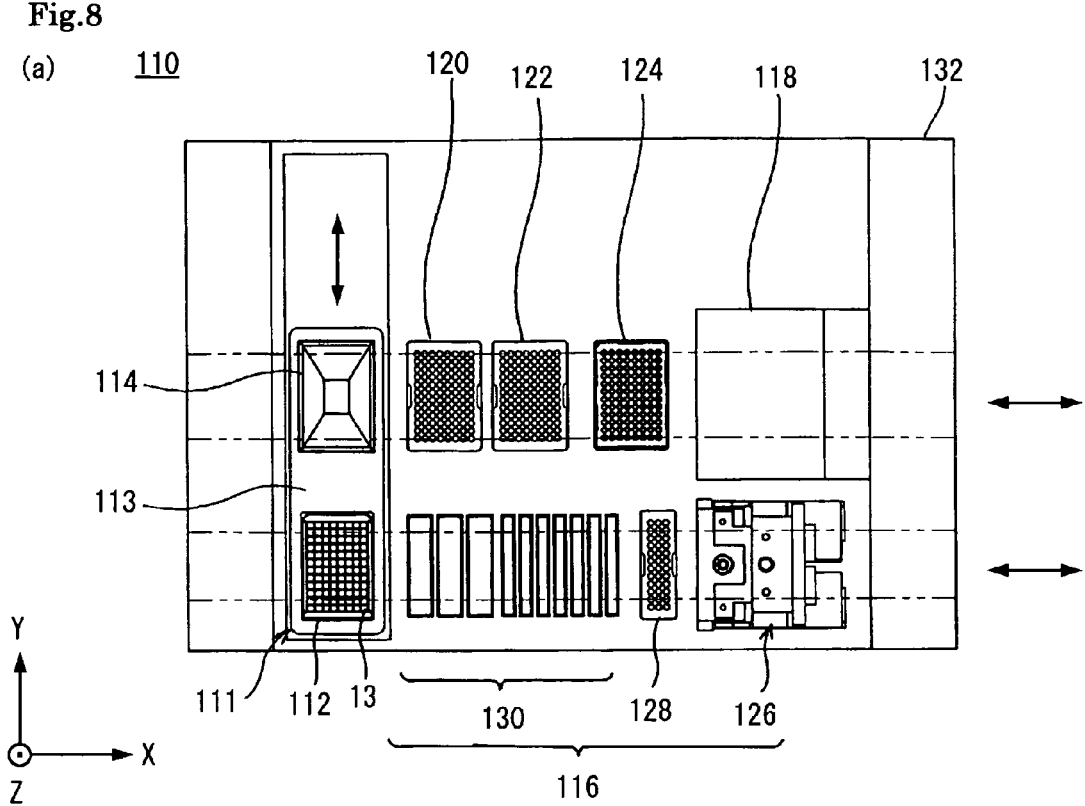
FIG. 8 is a plan view of a magnetic particle parallel processing apparatus permitting repeated use of a container according to a second embodiment of the present invention.
Figure 8:
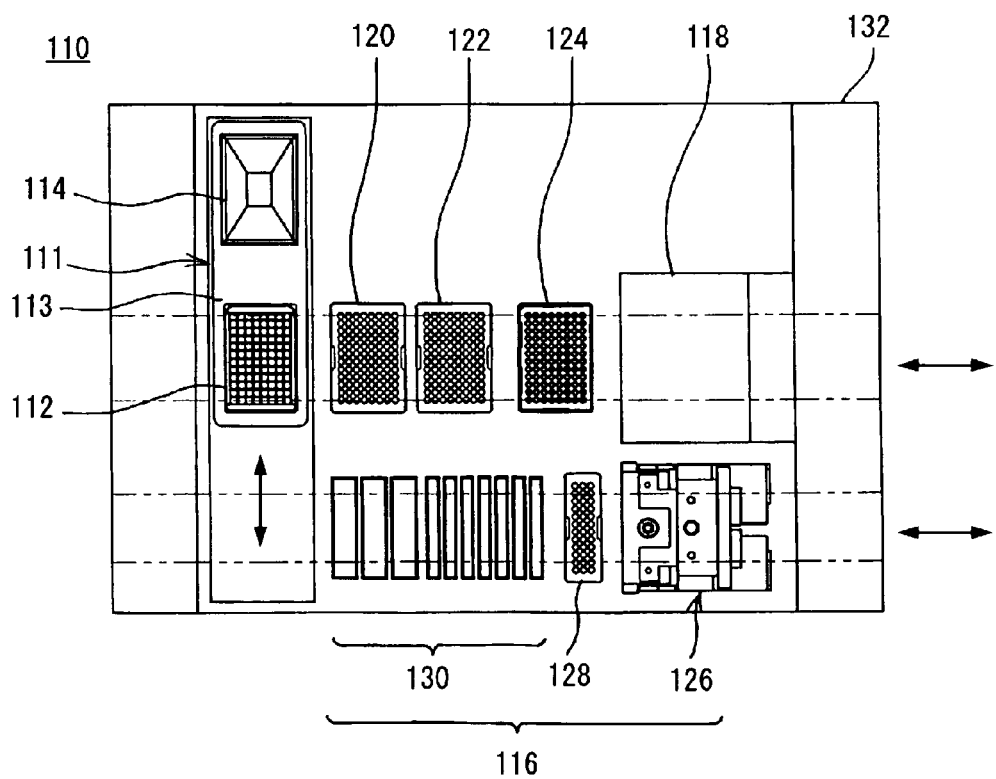
Figure 9:
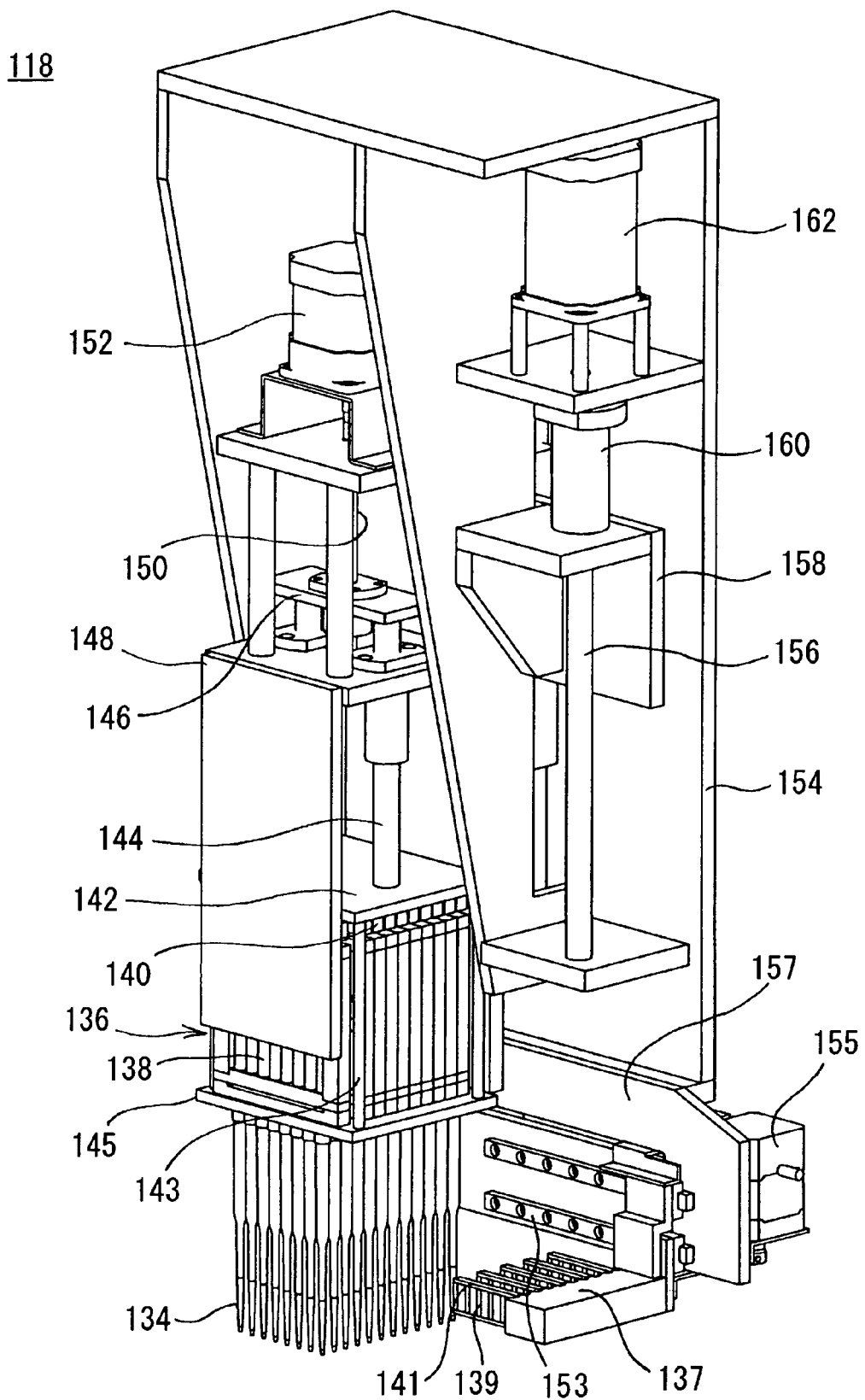
FIG. 9 is a perspective view of a magnetic separator according to the second embodiment of the present invention.
Figure 10:
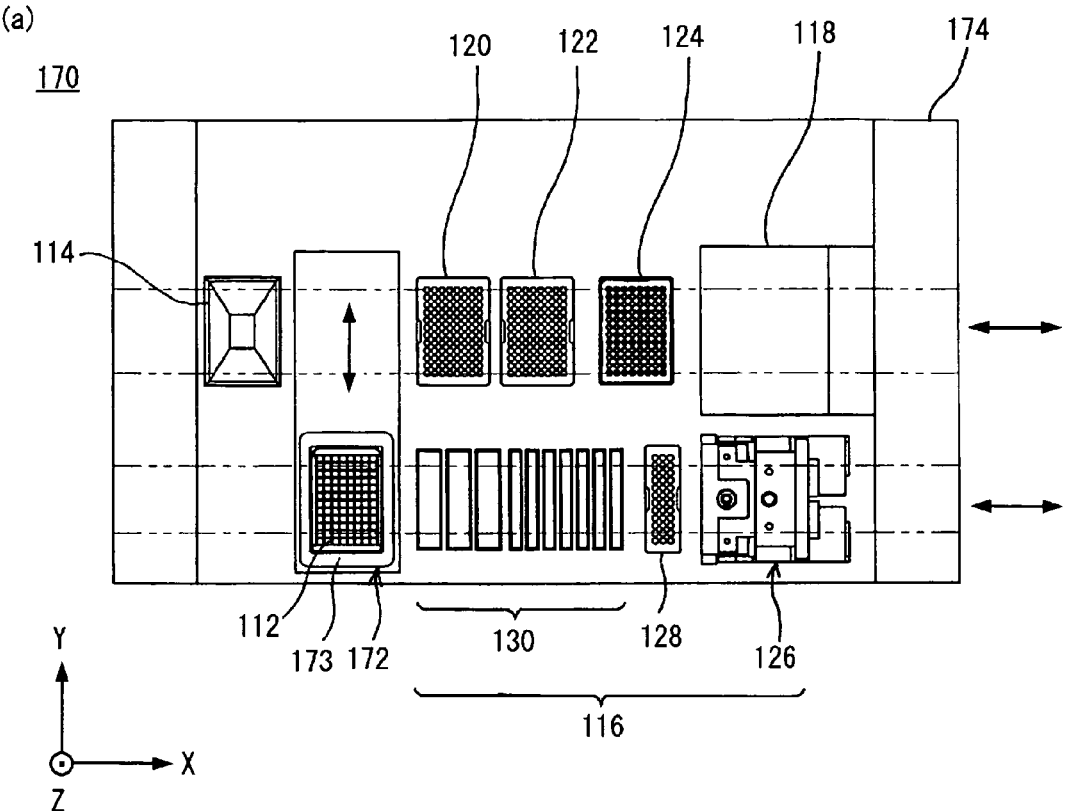
FIG. 10 is a plan view of a magnetic particle parallel processing apparatus permitting repeated use of a container according to a third embodiment of the present invention.
Figure 10:
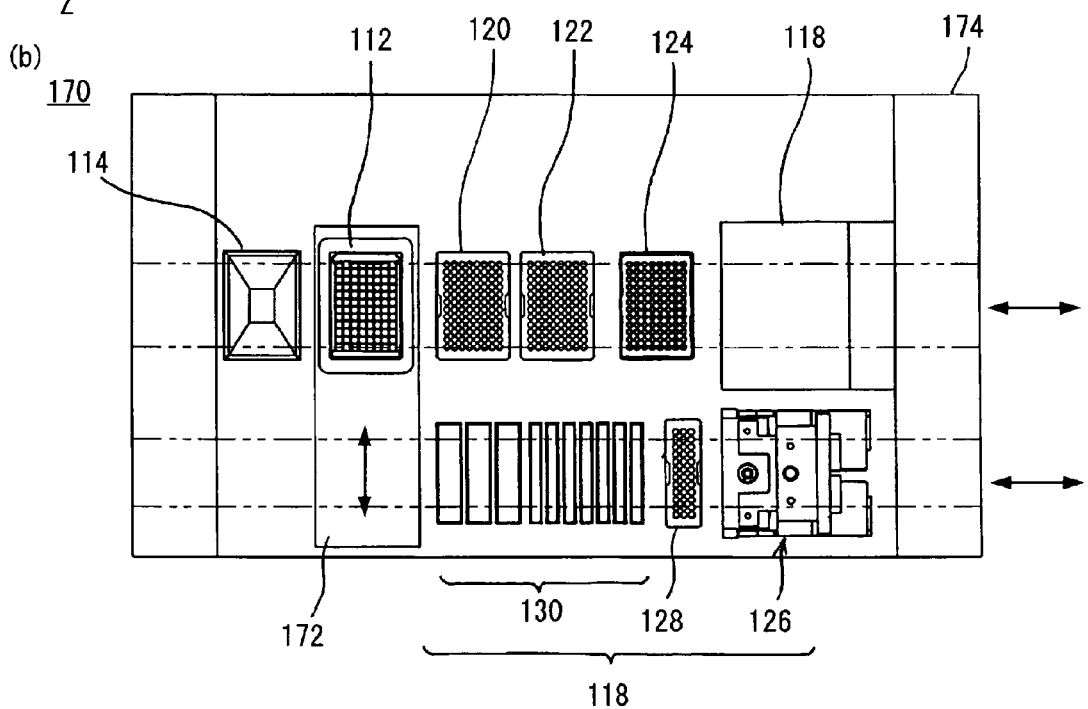

BRIEF DESCRIPTION OF THE REFERENCE SYMBOLS 10, 110, 170: Magnetic particle parallel processing apparatus permitting repeated use of a container
12, 112: Reaction container
14, 114: Liquid disposal tank
16, 116: Reagent etc. feeder
18, 118: Magnetic separator
19, 130: Reagent etc. storage unit
38, 48, 134: Dispensing tip
11, 111: Processing carriage
30: Feeding carriage
74, 137: Magnet support (magnetic means)

The invention claimed is:

1. A magnetic particle parallel processing apparatus permitting repeated use of a container, comprising:
at least one reaction container capable of storing a liquid to be processed;
a liquid disposal tank capable of storing a liquid to be disposed or allowing the liquid to pass through;
a reagent feeder with at least one flow channel for feeding at least one type of liquid selected from the group consisting of two or more types of solutions and a magnetic particle suspension according to the processing content, at a given amount and at a given timing, to said reaction container;
and a magnetic separator which has at least one processing nozzle with a distal end insertable into said reaction container and said liquid disposal tank, for sucking and discharging a liquid through said distal end, and which also has a magnetic means capable of applying a magnetic field to the interior of the distal end to thereby attract magnetic particles contained in the liquid inside the distal end to the inner wall thereof to effect separation of the magnetic particles, and canceling the magnetic field to thereby release the attracted magnetic particles and re-suspend the same in a liquid, wherein the distal end of said processing nozzle is relatively movably provided between said reaction container and said liquid disposal tank,
said flow channel has a distal end insertable into said reaction container, the solutions and the magnetic particle suspension are discharged through the distal end, and the distal end of the flow channel is relatively movably provided with respect to the reaction container, and
when the distal end of the processing nozzle is moved to a position where it is insertable into the liquid disposal tank, the distal end of the flow channel can be moved to a position where it is insertable into the reaction container while the distal end of the processing nozzle remains in the position where it is insertable into the liquid disposal tank.

2. A magnetic particle parallel processing apparatus permitting repeated use of a container according to claim 1, wherein said reagent feeder has two or more reagent storage units for previously storing various solutions and a magnetic particle suspension required for processing.

3. A magnetic particle parallel processing apparatus permitting repeated use of a container according to claim 1, wherein
said reaction container is provided on a transfer pathway of the distal end of said flow channel, and said reaction container and said liquid disposal tank are provided on a transfer pathway of the distal end of said processing nozzle.

4. A magnetic particle parallel processing apparatus permitting repeated use of a container according to claim 1, wherein
said reaction container and said liquid disposal tank are movably provided with respect to the distal end of said processing nozzle, and said reaction container is capable of passing through a feeding position on the transfer pathway of the distal end of said flow channel.

5. A magnetic particle parallel processing apparatus permitting repeated use of a container according to claim 1, wherein
said reaction container and said liquid disposal tank are provided in a processing carriage capable of reciprocating movement along a straight line with respect to the distal end of said processing nozzle.

6. A magnetic particle parallel processing apparatus permitting repeated use of a container according to claim 1, wherein
said reaction container is movably provided between a processing position on a transfer pathway of the distal end of said processing nozzle and a feeding position on a transfer pathway of the distal end of said flow channel.

7. A magnetic particle parallel processing apparatus permitting repeated use of a container according to claim 1, wherein
an inside bottom of said reaction container is formed so that a liquid can be sucked and discharged even though the distal end of said processing nozzle abuts thereon.

8. A magnetic particle parallel processing apparatus permitting repeated use of a container according to claim 7, wherein
a gap portion having a width narrower than an aperture diameter of said distal end, and a length longer than the aperture diameter of the distal end, is formed in a vicinity of the center of the inside bottom of said reaction container.

9. A magnetic particle parallel processing apparatus permitting repeated use of a container according to claim 1, wherein
a water absorbent portion is provided in a rim of the opening of said liquid disposal tank.

10. A method of magnetic particle parallel processing permitting repeated use of a container comprising:
a suspension storing step for storing a first liquid obtained by feeding through a distal end of a flow channel of a reagent feeder a magnetic particle suspension to at least one reaction container;
a whole amount suction step for sucking the whole amount of said first liquid stored in the reaction container by inserting at least one distal end of a magnetic separator which has at least one processing nozzle with the distal end for sucking and discharging a liquid through the distal end, and which also has a magnetic means capable of applying a magnetic field to the interior of the distal end, into said reaction container;
a whole amount discharging/feeding step for discharging the whole amount of the residual first liquid from the distal end into a liquid disposal tank in a state where said magnetic particles are attracted to the inner wall of the distal end of said processing nozzle by applying a magnetic field to said distal end, and for feeding a second liquid into said reaction container in parallel with the discharging operation; and
a magnetic particle contacting step for contacting said magnetic particles with said second liquid by inserting the distal end of said processing nozzle into said reaction container and sucking second liquid, wherein
said suspension storing step, said whole amount suction step, and said whole amount discharging/feeding step are performed by relatively moving the distal end of said flow channel with respect to said reaction container, and by relatively moving said reaction container and said liquid disposal tank with respect to the distal end of said processing nozzle, and said whole amount discharging/feeding step is performed by, when the distal end of the processing nozzle is moved to a position where it is insertable into the liquid disposal tank, moving the distal end of the flow channel to a position where it is insertable into the reaction container while the distal end of the processing nozzle remains in the position where it is insertable into the liquid disposal tank.

11. A method of magnetic particle parallel processing permitting repeated use of a container according to claim 10, wherein
in said contacting step the magnetic particles are contacted with said second liquid by re-suspending the magnetic particles in said second liquid in a state where the magnetic field is cancelled, or by sucking/discharging the second liquid while the magnetic particles are being attracted in a state where the magnetic field is applied.

12. A method of magnetic particle parallel processing permitting repeated use of a container according to claim 10, wherein
said first liquid containing the magnetic particle suspension or said second liquid is discharged from the reagent etc. storage unit which stores solutions constituting said first liquid and said second liquid, and the magnetic particle suspension, through a distal end of at least one flow channel of the reagent etc. feeder, by inserting the distal end of said flow channel into said reaction container at once.

13. A method of magnetic particle parallel processing permitting repeated use of a container according to claim 10, wherein
said first liquid in said whole amount suction step is replaced with said second liquid, said first liquid in the whole amount discharging/feeding step is replaced with said second liquid, and said second liquid in the whole amount discharging/feeding step and in the magnetic particle contacting step is replaced with a third liquid.

14. A method of magnetic particle parallel processing permitting repeated use of a container according to claim 10, wherein
an inside bottom of said reaction container is formed so that a liquid can be sucked and discharged even though the distal end abuts thereon, and said whole amount suction step is performed by sucking in a state where said distal end is abutted on the inside bottom of said reaction container.

15. A method of magnetic particle parallel processing permitting repeated use of a container according to claim 14, wherein
said suspension storing step, said whole amount discharging/feeding step, and said whole amount suction step are performed by moving the distal end of the flow channel with respect to said reaction container, and by moving said reaction container and said liquid disposal tank with respect to the distal end of said processing nozzle.

16. A method of magnetic particle parallel processing permitting repeated use of a container according to claim 10, wherein
said suspension storing step, said whole amount discharging/feeding step, and said whole amount suction step are performed by moving said reaction container between a processing position on a transfer pathway of the distal end of said processing nozzle and a feeding position on a transfer pathway of the distal end of said flow channel.

* * * * *